US008580496B2

(12) United States Patent
Sotiriou et al.

(10) Patent No.: US 8,580,496 B2
(45) Date of Patent: Nov. 12, 2013

(54) METHOD AND KIT FOR THE DETECTION OF GENES ASSOCIATED WITH PIK3CA MUTATION AND INVOLVED IN PI3K/AKT PATHWAY ACTIVATION IN THE ER-POSTITIVE AND HER2-POSITIVE SUBTYPES WITH CLINICAL IMPLICATIONS

(75) Inventors: Christos Sotiriou, Uccle (BE); Sherene Loi, Brussels (BE); Grant McArthur, Camberwell (AU); Benjamin Haibe-Kains, Brussels (BE)

(73) Assignee: Universite Libre de Bruxelles, Brussels (BE)

( * ) Notice: Subject to any disclaimer, the term of this patent is extended or adjusted under 35 U.S.C. 154(b) by 132 days.

(21) Appl. No.: 12/860,638

(22) Filed: Aug. 20, 2010

(65) Prior Publication Data
US 2011/0038862 A1    Feb. 17, 2011

Related U.S. Application Data

(63) Continuation-in-part of application No. PCT/EP2009/052043, filed on Feb. 20, 2009.

(60) Provisional application No. 61/030,450, filed on Feb. 21, 2008.

(51) Int. Cl.
*C12Q 1/68* (2006.01)

(52) U.S. Cl.
USPC .......................................................... 435/6.1

(58) Field of Classification Search
None
See application file for complete search history.

(56) References Cited

U.S. PATENT DOCUMENTS

2005/0186577 A1   8/2005 Wang
2007/0172844 A1   7/2007 Lancaster et al.

FOREIGN PATENT DOCUMENTS

| WO | WO 2005/021788 A1 | 3/2005 |
| WO | WO 2005/071419 A2 | 8/2005 |
| WO | WO 2006/119593 A1 | 11/2006 |
| WO | WO 2007/109026 A2 | 9/2007 |

OTHER PUBLICATIONS

Dressman et al (Clin Cancer Research, 2006, 12(3 Pt 1): 819-826).*
Berns et al (Cancer Cell, 2007, 12(4): 395-402).*
Chollet et al (Clin Breast Cancer, 2006, 7(4): 336-338).*
Teschendorff et al., "A consensus prognostic gene expression classifier for ER positive breast cancer," *Genome Biology* (2006) 7: R101.
Whyte et al., "Correlation of PIK3Ca mutations with gene expression and drug sensitivity in NCI-60 cell lines," *Biochemical and Biophysical Research Communications* (2006) 340: 469-475.
Chang et al., "Gene expression signature of fibroblast serum response predicts human cancer progression: Similarities between tumors and wounds," *PLoS Biology* (2004) 2 (2): 0206-0214.
Farmer et al., "A stroma-related gene signature predicts resistance to neoadjuvant chemotherapy in breast cancer," *Nature Medicine* (2009) 15 (1): 68-74.
Ivshina et al., "Genetic reclassification of histologic grade delineates new clinical subtypes of breast cancer," *Cancer Res.* (2006) 66 (21): 10292-10301.
Naderi et al., "A gene-expression signature to predict survival in breast cancer across independent data sets," *Oncogene* (2007) 26: 1507-1516.
Pawitan et al., "Gene expression profiling spares early breast cancer patients from adjuvant therapy: derived and validated in two population-based cohorts," *Breast Cancer Research* (2005) 7: R953-R964.
Paik et al., "Gene expression and benefit of chemotherapy in women with node-negative, estrogen receptor—positive breast cancer," *Journal of Clinical Oncology* (2006) 24 (23): 3726-3734.
Loi et al., "Definition of clinically distinct molecular subtypes in estrogen receptor-positive breast carcinomas through genomic grade," *Journal of Clinical Oncology* (2007) 25 (10): 1239-1246.
Miller et al., "An expression signature for p53 status in human breast cancer predicts mutation status, transcriptional effects, and patient survival," *PNAS* (2005) 102 (38): 13550-13555.
Paik et al., "A multigene assay to predict recurrence of tamoxifen-treated, node-negative breast cancer," *The New England Journal of Medicine* (2004) 351 (27): 2817-2826.
Perou et al., "Molecular portraits of human breast tumors," *Nature* (2000) 406: 747-752.
Sorlie et al., "Gene expression patterns of breast carcinomas distinguish tumor subclasses with clinical implications," *PNAS* (2001) 98 (19) :10869-10874.
Van De Vijver et al., "A gene-expression signature as a predictor of survival in breast cancer," *New England Journal of Medicine* (2002) 347 (25): 1999-2009.
Sotiriou et al., "Gene expression profiling in breast cancer: Understanding the molecular basis of histologic grade to improve prognosis," *Journal of the National Cancer Institute* (2006) 98 (4): 262-272.
Wang et al., "Gene-expression profiles to predict distant metastasis of lymph-noe-negative primary breast cancer," *The Lancet* (2005) 365: 671-679.
van't Veer et al., "Gene expression profiling predicts clinical outcome of breast cancer," *Nature* (2002) 415: 530-536.
Sotiriou et al., "Breast cancer classification and prognosis based on gene expression profiles form a population-based study," *PNAS* (2003) 100 (18): 10393-10398.
Tokunaga et al., "The association between Akt activation and resistance to hormone therapy in metastatic breast cancer," *European Journal of Cancer* (2006) 42: 629-635.
Villeneuve et al., "cDNA microarray analysis of isogenic paclitaxel- and doxorubicin-resistant breast tumor cell lines reveals distinct drug-specific genetic signatures of resistance," *Breast Cancer Research and Treatment* (2006) 96: 17-39.
Stemke-Hale et al., "An integrative genomic and proteomic analysis of PIK3CA, PTEN, and AKT mutations in breast cancer," *Cancer Res.* (2008) 68 (15): 6084-6091.
Whitfield et al., "Common markers of proliferation," *Nature Reviews | Cancer* (2006) 6: 99-106.

(Continued)

*Primary Examiner* — Sean Aeder
(74) *Attorney, Agent, or Firm* — Merchant & Gould P.C.

(57) ABSTRACT

A method to determine the clinical outcome of breast tumor affecting a patient if treated with an antitumoral agent against breast tumor. The method includes the step of assaying a sample of a breast tumor from the patient for an expression level of selected genes, by contacting mRNA sequences from the cells of this breast tumor with a set of more than 3 nucleotide sequences related to human mutated PIK3CA.

23 Claims, 3 Drawing Sheets

(56) References Cited

OTHER PUBLICATIONS

Isakoff et al., "Breast cancer-associated PIK3CA mutations are oncogenic in mammary epithelial cells," *Cancer Res.* (2005) 65 (23): 10992-11000.

Desmedt et al., "Strong time dependence of the 76-gene prognostic signature for node-negative breast cancer patients in the TRANSBIG multicenter independent validation series," *Clin. Cancer Res.* (2007) 13 (11): 3207-3214.

Farmer et al., "Identification of molecular apocrine breast tumors by microarray analysis," *Oncogene* (2005) 24: 4660-4671.

Clark et al., "Constitutive and inducible AKT activity promotes resistance to chemotherapy, trastuzumab, or tamoxifen in breast cancer cells," *Molecular Cancer Therapeutics* (2002) 1: 707-717.

Noh et al., "Activation of the mTOR signaling pathway in breast cancer and its correlation with the clinicopathologic variables," *Breast Cancer Res. Treat.* (2008) 110: 477-483.

Oh et al., "Estrogen-regulated genes predict survival in hormone receptor-positive breast cancers," *Journal of Clinical Oncology* (2006) 24 (11): 1656-1664.

Rodriguez et al., "BRCA1 gene expression signature predicts for anthracycline-chemosensitivity in triple-negative breast cancer," *Current Cancer Research* (2009) 6039: 1-2. Abstract Only.

Sorlie et al., "Repeated observation of breast tumor subtypes in independent gene expression data sets," *PNAS* (2003) 100 (14): 8418-8423.

\* cited by examiner

PIK3CA signature (Tamoxifen-treated population)

PIK3CA signature Luminal subtype
(Tamoxifen-treated population)

PIK3CA signature
(ER+, HER2- untreated population)

PIK3CA signature, Luminal subtypes
(ER+, HER2- untreated population)

METHOD AND KIT FOR THE DETECTION OF GENES ASSOCIATED WITH PIK3CA MUTATION AND INVOLVED IN PI3K/AKT PATHWAY ACTIVATION IN THE ER-POSTITIVE AND HER2-POSITIVE SUBTYPES WITH CLINICAL IMPLICATIONS

This application is a Continuation-in-Part Application of PCT/EP2009/052043, filed Feb. 20, 2009, which claims benefit of Ser. No. 61/030,450, filed Feb. 21, 2008 in the USA and which applications are incorporated herein by reference. To the extent appropriate, a claim of priority is made to each of the above disclosed applications.

FIELD OF THE INVENTION

The present invention is related to a new detection method and a new detection kit of genes associated with PIK3CA mutation(s) and involved in PIK3/AKT pathway activation in the (luminal-B) ER-positive or HER2 positive subtypes with clinical implications. The present detection method and kit have a predictive clinical outcome (survival outcome) and could be therefore used for identifying if a patient from which this tumour sample is obtained could be submitted to a specific antitumoural treatment, especially to a tamoxifen or Herceptin treatment (or not). The present invention is also directed to the therapeutic application of a class of active compounds to be applied efficiently to the subtype of cancer detected by this method.

BACKGROUND OF THE INVENTION

Breast cancer (BC) may be subdivided into subgroups depending on expression profile of several genes and/or protein.

Her2 over expression in tumours results into a worse prognosis. BC patients having Her2 positive status are preferably not treated with anti oestrogens, but with anti Her2 drugs, such as Trastuzumab (Herceptin).

For the BC patients whose tumours express ER receptor (ER group) but do not over express Her2, the over expression of several genes related to proliferation results into the classification into the luminal B subgroup, with a worse prognosis. These luminal B patients are preferably not treated with anti-oestrogens, but with more aggressive treatments (chemotherapy).

Deregulated phosphatidylinositol 3-kinase (PI3K)-AKT signaling has been implicated in many hallmarks of carcinogenesis as the pathway influences multiple aspects of cell physiology. Many genomic alterations act on this pathway, activating its signaling activity, which contributes to tumor progression, metastases and resistance to treatment.

PI3Ks are heterodimeric lipid kinases for which the p110α catalytic and regulatory p85 subunits are encoded by separate genes. In breast cancer, mutations of the PIK3CA gene, which codes for the p110α catalytic subunit, has been found in 18-40% of human cancers, which makes it one of the most common genetic changes in breast cancer beside p53 mutations and HER2 amplification. Expression of p110α mutants in human mammary epithelial cells induces multiple phenotypic alterations characteristic of breast tumor cells and in vivo studies with cells expressing PIK3CA mutants result in a more active PI3K pathway and induction of tumors. The lack of a homogeneous population makes it difficult to investigate the prognostic or predictive effect of PIK3CA mutations in breast cancer. Extensive cross-talk at multiple levels with other pathways both upstream and downstream of PI3K also makes the exact role of PIK3CA mutations in breast cancer difficult to elucidate.

Mutations in the AKT1 pleckstrin homology domain (PHD) reported in breast cancer at a frequency of 8% may result in PI3K-independent membrane recruitment and activation of AKT1 and downstream signaling. The clinical relevance of this mutation is unknown.

Given the complexity of PI3K signaling, it is important to have molecular markers that can predict for prognosis and therapeutic response for incorporation into future breast cancer clinical trials with compounds that act on this pathway.

As the Kaplan-Meier analysis of the PIK3CA mutation versus the wild-type patients did not reveal any statistically significant differences in prognosis, mutation status alone may not be a sensitive marker of significant activation of the PI3K/AKT pathway that would affect tumor progression. Other downstream interactions of an extra oncogenic "hit" may be required.

AIMS OF THE INVENTION

A first aim of the present invention is to propose a new detection method and new detection means (kit) of improving clinical outcome (especially survival outcome) of a human patient following application of this detection method upon a tumour sample obtained from this patient and the defining (selecting among known treatments) the most effective treatment that could be applied to this patient.

In particular, the present invention aims to provide such detection method and kit which allows a better discrimination of clinical outcome of patients with ER-positive and/or HER2-positive sub-types tumour samples and to identify which type of patients should receive (be prescribed) an anti oestrogen, more preferably a tamoxifen or aromatase inhibitor therapy or Herceptin related therapy or hormone/chemo, radio- or immunotherapy.

SUMMARY OF THE INVENTION

The present invention is related to a method and a kit for a detection of mutated PIK3CA gene and/or mutated AKT-1 gene and/or gene(s) involved PIK3/AKT pathway activation (s) in (especially in high proliferative luminal-B) ER-positive [BC] or HER2-positive subtype tumour sample as described in the enclosed set of claims.

The inventors have investigated frequency, phenotype and clinical relevance associated with PIK3CA or AKT-1 mutations in a large homogenous data set of ER+(BC), tamoxifen-only treated breast tumours. The inventors have examined the associated gene expression profiles to further understand the biology associated with PIK3CA or AKT-1 mutations when they activate the PI3K/AKT pathway.

The inventors have selected a preferred gene set related to mutated PIK3CA and/or AKT, comprising the 81 genes of Table 2a or the 65 genes of Table 2b, more preferably the 38 genes of Table 4.

The inventors have selected an alternative preferred gene set related to mutated PIK3CA and/or AKT, comprising the 278 genes of Table 5 or, more preferably, the 14 genes of Table 6.

The inventors further found other (isolated) genes associated with mutated PIK3CA and/or Akt mutations, advantageously, 1, 2, 3, 4, 5, 6, 7, 8, 9, 10, 11 or all the 12 genes selected from the group consisting of the following genes: PML (Entrez gene ID 5371), PP2A (Entrez gene ID 5523, 5525, 5526), IRS2 (Entrez gene ID 8660), PIK3R1 (Entrez gene ID 5295), ESR1 (Entrez gene ID 2099), FOXO3A (Entrez gene ID 2309), P21 (PAK2) (Entrez gene ID 5062), RPS6K (Entrez gene ID 6198), EIF4E (Entrez gene ID 1977), RHEB (Entrez gene ID 6009), P27 (Entrez gene ID 1785), PI3K (Entrez gene ID 18708) and possibly their isoforms or variants.

The use of the gene set(s) or of the method according to the invention allows an efficient establishment of PIK3CA mutated signature and the use of these gene sets or of the method according to the invention allows accurate and sensitive determination of the state of activation of the PI3K/AKT pathway, similar to that induced by a PIK3CA or a AKT1 mutation.

The present invention is further related to a method to determine the clinical outcome (preferably the survival outcome) of a (breast) tumour affecting a patient, if this patient is treated with an anti oestrogen agent against this (breast) tumour, this method comprising the step of assaying a sample of this breast tumour obtained from this patient for an expression level of one or more gene(s) or synthesis of corresponding protein(s) encoded by these gene(s), preferably more than 3, 4, 5, 6, 7, 8, 9, 10, 11, 12, 13, 14, 15, 16, 17, 18, 19 or 20 genes (including isoforms and variants) or proteins selected from the Table 2a, from mutated PIK3CA genes and proteins and/or from mutated AKT-1 genes or proteins involved in the PI3K/AKT pathway.

By one or more gene(s), it is meant 4, 5, 6, 7, 8, 9, 10, 15, 20, 25, 30, 35, 40, 45, 50, 55, 60, 65, 70, 75 and every number till 81 genes mentioned and identified in these tables 2a, 2b or 4, with every possible combination of selected genes (or corresponding proteins and fragments thereof).

The present invention is also related to a method to determine a prognosis and/or prediction of a response of a patient having a (breast) tumour to a treatment, if treated with an anti oestrogen agent against this (breast) tumour, and comprising the step of assaying for an expression level of one or more (preferably more than 3, 9, 10, 19 or all of the gene(s) or protein(s) of (Table 2a or Table 2b or Table 4 or Table 5 or of table 6), of mutated PIK3CA/AKT-1 genes or proteins or of genes or proteins involved in the PI3K/AKT pathway activation from a breast cancer cells obtained from a breast cancer tumour sample from the patient.

The method may also comprise a step of determining a clinical outcome, preferably a survival outcome correlated to an assaying step of the patient and/or a step of selecting an antitumoural compound, (especially an anti oestrogen agent), which could be administrated to this patient.

In the method according to the invention, the expression levels are indicative of probabilities of recurrence (or relapsing) of cancer, possibly through metastasis.

By anti oestrogen, it is meant the administration of a selective oestrogen receptor modulator (SERM), a selective oestrogen receptor down regulator (SERD), tamoxifen, raloxifene, faslodex, or a mixture thereof.

In the method according to the invention, the anti oestrogen agent against breast cancer is also any compound that could be used in hormonal therapy of cancer, preferably by administration of an efficient compound selected from the group consisting of a selective oestrogen receptor modulator (SERM), a selective oestrogen receptor down regulator (SERD), preferably tamoxifen, raloxifene, faslodex or a mixture thereof, GnRH analog or a aromatase inhibitor (AI) such as Letrozole, Anastrozle or Exemestane.

In the method according to the invention, the breast tumour is a HER2+ OR ER+(BC) tumour, especially a luminal-B ER+ tumour evidenced by high expression of proliferative genes.

By HER2-positive, it is meant HER2 over expression. This status is measured at gene level {i.e. amplification}, at mRNA level or at the protein level and wherein this over expression in BC tumours results into a worse prognosis.

BC patients having HER2 positive status are generally not treated with anti oestrogens as they are relatively resistant to their effects.

By luminal B, it is meant a highly proliferative tumour (ER+ and Her2−), preferably demonstrated using published prognostic gene expression profiles such as GGI, Oncotype Dx, Intrinsic gene set, Amsterdam 70-gene signature, Rotterdam 76-gene signature, Wound-response signature or having KI67 high expression (>5%).

Luminal B represents a worse prognosis. These luminal B patients are generally not treated with anti-oestrogens alone.

In the method of the invention, the step of assaying for the expression level of one or more gene(s), protein(s) or portions thereof comprises a detection of target nucleic acids prepared by a mRNA amplification from the sample, by a detection of (the amplified) target nucleic acids from the sample, by a quantitative PCR, (preferably a qRT PCR), by a detection of corresponding target proteins or their fragments through specific binding with corresponding capture antibodies or similar capture molecules (nanobodies, specific Hypervariable portions of antibodies, etc), preferably such detection of target proteins is obtained in patient blood or in breast cancer epithelial cells enriched from patient blood.

Advantageously, in the method according to the invention, the detected target genes or proteins are selected from the group consisting of more than 3 genes (9, or 15) or corresponding proteins of the genes presented in Table 2a, Table 2b or Table 4 (or Table 5 or 6) or genes involved in PI3K/AKT pathway activation.

Advantageously, at least one gene selected from the group comprising PFN2, ORC5L, MYC, E2F5, ARPP19 and MNAT1 (the first group of these genes being under expressed in PIK3CA mutated subjects) and at least one gene selected from the group comprising SCGB2A2, NOTCH2, TNIK, GOLPH2, ARHGDIB, GALNT2, SPTLC2 and SCGDAD2 (these genes of the second group being over expressed in PIK3CA mutated subjects), wherein at least three gene are selected.

In the method according to the invention, the sample could be obtained by various techniques, preferably by biopsy, more preferably by a minimally invasive technique or selected from core biopsy, excisional biopsy, ductal lavage simple, a fine needle aspiration sample or from cells micro dissected from the sample.

Another aspect of the present invention is related to a set of capture nucleotide sequences comprising one or more strand(s) of sufficient length of about 15 to about 250 or more nucleotides for obtaining an efficient and specific hybridization of corresponding target nucleotide sequences (RNA sequences) of human mutated PIK3CA/AKT-1 sequences or sequences involved in PI3K/AKT pathway activation, especially one or more sequence(s) of Table 2a, Table 2b or Table 4 or capture molecules (antibodies, etc) that may bind specifically these corresponding target proteins, wherein at least a portion of this set is hybridized to nucleotides quantitatively amplified from RNA sequences of breast cells.

Advantageously, the set of capture nucleotide sequences or capture molecules that may bind the proteins is immobilised on a solid support surface as a microarray.

Preferably, (specific) hybridisation between capture and target sequences is obtained under stringent conditions (under conditions well-known to the person skilled in the art, for instance, the one described by SAMBROOK ET AL) which provides sufficient binding efficiency of the target sequences on their specific capture probes to the detected with no or very low, preferably lower than 5% and even lower than 1%, cross-hybridization on non-related target capture probes.

Advantageously, the hybridized target nucleotide sequences are previously amplified from RNA sequences of breast cells.

Advantageously, the breast tumour cell is ER+(BC) or HER2+ tumour cells.

A further aspect of the present invention is related to this set, wherein the mutated genes comprise mutation(s) in the PIK3CA mutated sequences are PIK3CA mutations selected from a group consisting of A3140G, A3150T in EXON20 of the genomic DNA and/or G1633A, G1624A or G1634A in EXONS of the genomic DNA and corresponding nucleotide of messenger RNA sequence.

More preferably, the set according to the invention comprises more than 3, 5, 10, 15 or all the sequences selected from the group consisting of the sequences above-described and present in a Table 2a, Table 2b or Table 4 or present in Tables 5 or 6.

Advantageously, the set according to the invention may also further comprise one or more genes selected from the group consisting of IL17BR (55540), CHDH (55349), QPRT (23475), HOXB13 (10481) genes wherein over expression of IL17BR and/or CHDH sequences and/or under expression of QPRT and/or HOXN13 sequences are negative prognosis of selective oestrogen receptor modulator SERM treatment of oestrogen receptor positive patient.

Another aspect of the invention is identifying a subgroup of Her2 positive breast cancer (patients) having the signature of mutated PIK3CA (preferably identified by the method of the invention), that would benefit from anti oestrogen treatment Another aspect of the invention is therefore anti oestrogen for use in the treatment of Her2 positive breast cancer (patients) having the signature of mutated PIK3CA and being preferably identified by the method of the invention.

Another aspect of the invention is anti oestrogen for use in the treatment of ER positive, luminal B breast cancer (patients) having the signature of mutated PIK3CA.

The method and kit according to the invention could be also combined with one or more detection method, kit and tools already described in the state of the art especially in the document WO 2006/119593, especially prognostic means (signature) or gene list (gene set) which could be used for an efficient prognosis (prognostic) of cancer in ER+ patient, but also possibly in ER− patient such as the one described by WANG ET AL. (2005), LANCET 365, page 671-679, VAN 'T VEER ET AL. (2002), Nature 415, pages 530-536, PAIK ET AL. (2004) New ENGL. J. MED. 351, pages 2817-2826, TESCHENDORF ET AL. (2006). Genome Biol. 7, R101 206, VAN DE VIJVER ET AL. (2002) New ENGL. J. MED. 347, pages 1999-2009, PEROU ET AL. (2000) Nature, 406, pages 747-752, SOTIRIOU ET AL (2003) PNAS100, pages 10393-10398, SORLIE ET AL. (2001) PNAS 98, pages 10869-10874, MILLER ET AL. (2005) PNAS102, pages 13550-13555, NADERI ET AL. (2007) Oncogene 26, pages 1507-1516, PAIK ET AL. (2006) J. Clin. Oncol. 24, pages 3726-3734, SOTIRIOU ET AL. (2006) J. Natl. Cancer Inst., 98, pages 262-272, CHANG ET AL. (2004) PLOS BIOL 2: E7, SORLIE ET AL. (2003) PNAS100, pages 8418-8423, IVSHINA ET AL. (2006) Cancer Res. 66, pages 10292-10301, PAWITAN ET AL., (2005) Breast Cancer Res; 7: R953-964, FARMER ET AL. (2005) Oncogene 24, pages 4660-4671, WHITFIELD ET AL. (2006) Nat. Rev. Cancer 6, pages 99-106, and the expression profiling protein used in breast cancer as described in document WO2005/071419, the expression profiling protein/gene described in the document WO2005/021788. The set of the invention may also comprise or consist of capture nucleotide sequences or capture molecules that can bind specifically the proteins encoded by these genes of these nucleotide or proteins sets.

Another aspect of the present invention is related to a kit or device, preferably a computerised system comprising a bioassay module configured for detecting gene expression (or protein synthesis) from a tumour sample which is based upon the genes set including molecules that bind specifically the proteins encoded by these genes set according to the invention and a processor module configured to calculate expression (over or under expression) of these genes and/or synthesis of corresponding encoded proteins and to generate a clinical outcome, preferably a survival outcome and a risk assessment for a tumour sample (risk assessment to develop a malignant tumour) or susceptibility that a patient from which this tumour sample has been obtained could be treated by efficient therapeutic treatment, especially a treatment based upon the administration of an anti oestrogen, preferably tamoxifen. Advantageously, the generated set of genes (and proteins) according to the invention may also provide a detection of tumour correlated with a Herceptin (Trastuzumab Genentech, California USA) resistance in HER2 tumour samples. Therefore, the method of the invention could be used in patients presenting a HER2 subtype combined with this resistance for selecting an appropriate treatment that is not based upon administration of Herceptin to the patient The inventors have measured that the signature of the invention (mutated signature of PIK3CA and/or Akt) predicts for a better outcome of anti-oestrogen treatments of BC patients.

The inventors have measured that the signature of the invention (mutated signature of PIK3CA and/or Akt) predicts for a better outcome of anti-oestrogen treatments in luminal B BC patients.

The inventors have measured that luminal B BC patients having the mutated PIK3CA and/or Akt signature according to the invention benefit from anti-oestrogen treatments.

Surprisingly, the inventors have observed that the mutated signature of PIK3CA and/or Akt in ER+ and HER2+ BC patients predicts for a better outcome.

Surprisingly, the inventors have observed that the mutated signature of PIK3CA and/or Akt in ER+ (including for luminal B patients) and HER2 positive BC patients predicts for a better response to anti oestrogens, possibly in addition for Her2 positive BC patients of anti HER2 drugs, such as Herceptin (trastuzumab).

The inventors have therefore treated with anti oestrogen BC patients with the PIK3CA mutated signature identified according to the method of the invention.

The BC patients (with the PIK3CA mutated signature) treated (according to the invention) with anti oestrogen are preferably ER positive.

The BC patients (with the PIK3CA mutated signature) treated (according to the invention) with anti oestrogen are luminal B ER positive.

The BC (with the PIK3CA mutated signature) treated (according to the invention) with anti oestrogen are Her2 positive.

Conversely, the inventors have observed that chemotherapy is less effective in BC patients having the gene signature of mutated PIK3CA and/or Akt, according to the present invention.

The inventors have further observed that radiotherapy is less effective in BC patients having the gene signature of mutated PIK3CA and/or Akt, according to the present invention.

The inventors have further observed that PI3kinase/AKT/mTOR pathway inhibitors are less effective in BC patients having the gene signature of mutated PIK3CA and/or Akt, according to the present invention.

The method, gene(protein) set and kit (or tools) according to the invention could be also used for selecting an adequate therapeutic treatment to get apply to the patient from which the tumour sample has been obtained, especially selecting an appropriate dose and/or schedule of chemo-therapeutic and/or bio-pharmaceutical and/or targeted agent.
This treatment could be based upon administration of anti oestrogens, taxanes, anthracyclines, CHOP or other drugs like velcade, fluorouracil, uracil, vinblastine, gemcitabine, methotrexate, goserelin, irinotecan, thiotepa, topotecan, toremifene, anti-EGFR, anti-HER2/neu, anti-VEGF, RTK-inhibitor, anti-VEGFR, GRH, anti-EGFR/VEGF, HER2/neu, EGF-R or anti-HER2.

The method, set and kit according to the invention could be also used in combination with a method for controlling the efficiency of the treated method or an active compound in cancer therapy. Indeed, the method, set and kit (or tools) according to the invention that apply for an efficient prognostic of cancer in various breast cancer types could also be used for an efficient monitoring of the treatment applying to the patient suffering from this cancer.

The method according to the invention may require a first prognostic step which is applied to the patient before submitting the patient to a treatment or to a second diagnosis step following this treatment.

This method could be applied several times (two time, three times, four times, five times, etc) to the mammal subject (human patient) during the treatment or during the monitoring of the treatment several weeks (one week, two weeks, three weeks, four weeks, etc) or months (one month, two months, three months, etc) after the end of the treatment to reveal if a modification of gene expression or protein synthesis in a sample subject is obtained following the treatment.

DETAILED DESCRIPTION OF THE INVENTION

Figure Legends

FIG. 1 shows that there was no correlation between PIK3CA mutations and the luminal subtypes defined using the GG values, evidencing that PIK3CA mutations are not associated with either molecular ER-positive subtypes. In contrast, the inventors did surprisingly find an association between the expression levels of the associated PI3K mutation signature and the molecular subtypes. Indeed, higher levels of PI3K associated mutation signature were associated with the HER2 and luminal A low proliferate subtypes.

FIG. 2 presents a Kaplan-Meier analysis revealed that PIK3CA mutations were surprisingly not significantly associated with a better or worse prognosis compared with those tumours without a mutation. Analyses of exon 9 and 20 mutations separately did not change this result. Univariate survival analysis confirmed no significant correlation between PIK3CA mutations and prognosis.

Figure 5:
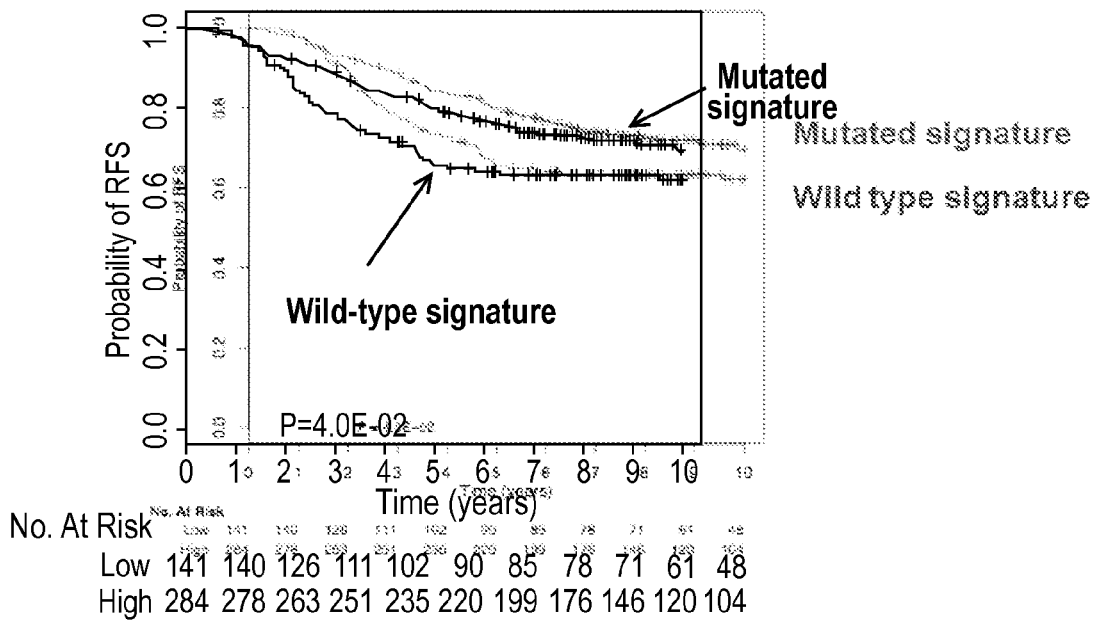

FIG. 5 presents results that are similar in the breast cancer patients who had received no systemic treatment and that the group of patients with higher expression levels of the PIK3CA mutation signature had better clinical outcome than those with lower expression levels as shown by this KM curve analysis.

Figure 6:
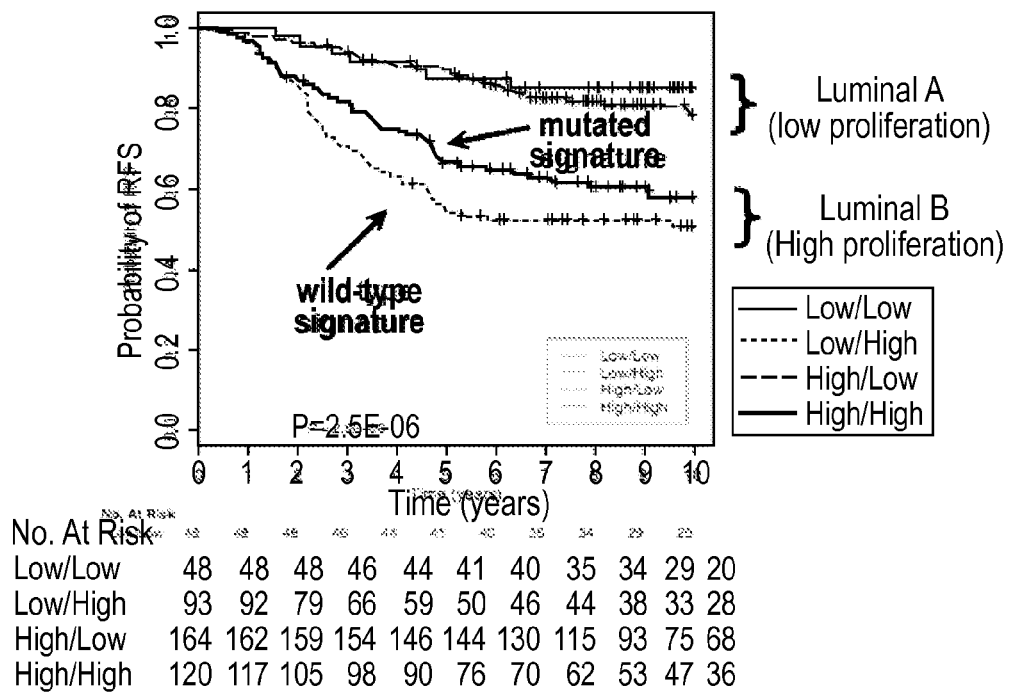

FIG. 6 shows the association between the expression levels of the PIK3CA signature and clinical outcome was only seen within the highly proliferative high risk luminal B tumours. Surprisingly, tumours with higher expression levels of the signature showed better clinical outcome than with lower expression levels.

MATERIALS AND METHODS

Tumour Samples Screened for Mutation Status

Primary breast cancer tumour samples from a previously described "tamoxifen-only treated" data set (Loi, 2007; J. Clin Oncol., 25, 1239-46;) were collected for DNA extraction and mutation analysis. The inventors obtained DNA from 173 samples for PIK3CA mutation sequencing and from 131 samples for AKT1 mutation analysis. The median follow-up of these samples was 9.0 yrs (range: 8.2-9.8 yrs), with 45 (28%) distant metastatic events.
Screening for Mutations
PIK3CA The vast majority (>85%) of PIK3CA mutations reported in human breast cancers are missense mutations clustering in exons 9 (E545K) and 20 (H1047R). (SAAL, 2005) These exons we screened for mutations using single strand conformation polymorphism (SSCP). The PIK3CA primer sets are as follows:

```
Exon 9:
Forward:{6FAM}TGAAAATGTATTTGCTTTTTCTGT;   SEQ ID N° 3

Reverse:{VIC}TGTAAATTCTGCTTTATTTATTCC;    SEQ ID N° 4

Exon 20:
Forward:{NED}TCCAAACTGACCAAACTGTTCTT;     SEQ ID N° 5

Reverse:{PE}TCCAGAGTGAGCTTTCATTTTCTC.     SEQ ID N° 6
```

Primers labeled with 5' fluorescence (Applied Biosystems). PCR was carried out with 10 ng of genomic DNA in a reaction volume of 10 μL, with the inclusion of 0.25 units Hot Star TaqDNA polymerase (QIAGEN, Valencia, Calif.). After an initial denaturation step of 95° C. for 10 minutes, a "touchdown" program was used consisting of 2 cycles of amplification at annealing temperatures of 63° C. to 59° C.; followed by 30 amplification cycles at an annealing temperature of 58° C. and a final extension cycle of 72° C. for 5 minutes. Samples were prepared for single-strand conformational polymorphism (SSCP) analysis using the ABI-3130 automated capillary sequencer. The sample, size standard and Hi-Di™ Formamide was mixed in each well of sample plate. The PCR-product was denatured for 3 minutes at 95° C. and then cooled on ice for minutes to avoid re-annealing of the complementary strands before being run using the Genemapper fragment analysis module on ABI 3130 genetic analyzer. Labelled fragments are visualized on an Applied Biosystems DNA analyzer. The genescan LIZ® size standard was used in all samples as an internal ladder to align data from different capillaries and eliminate capillary-to-capillary or run-to-run variability. Cases showing aberrant peak shifts by SSCP were reamplified and sequenced directly with the BigDye terminator method (Applied Biosystems; Warrington, United Kingdom or Forster City, Calif.) on an auto sequencer (ABI PRISM 3100).
AKT1

The mutation screening for AKT1 exon 4 was carried by High-Resolution Melting (HRM) analysis. These exons were screened for mutations using capillary electrophoresis single strand conformation polymorphism (CESSCP)
The AKT1 primer sets are as follows:

```
Exon 4
Forward: AGGGTCTGACCCCTAGAGATG    SEQ ID N° 1

Reverse: AGAGGGCTCCAGCCAACC       SEQ ID N° 2
```

PCR was carried out with 15 ng of genomic DNA in a reaction volume of 10 µL, including 5 µL of the High-Resolution Melting Master (Roche) for amplification and detection of heteroduplex regions in PCR amplicons. The High-resolution melting master contains a dye, ResoLight that enables detection of double-stranded DNA by fluorescence, monitoring formation of amplicons during PCR cycling, and melt curve analysis. Samples were carried out in duplicate, in a 96-well plate. After an initial denaturation step of 95° C. for 15 minutes, a touch-down program was used consisting of 2 cycles of amplification at annealing temperatures of 63° C. to 59° C.; followed by 55 amplification cycles at an annealing temperature of 58° C. and a final Melt from 70° C. to 95° C. PCR cycling and HRM analysis was performed on the Light Cycler 480 (Roche Diagnostics; F. Hoffmann-La Roche Ltd.). LightCycler480 Software (v1.3.0.0705) was used to analyse results. Samples with variations in DNA sequence are distinguished by discrepancies in melting curve shape. Samples showing deviations in melt curve were treated with ExoSapIT (GE Healthcare, Buckinghamshire, England) according to the manufacturer's instructions and sequenced directly with the BigDye terminator method (Applied Biosystems; Warrington, United Kingdom or Forster City, Calif.) on an auto sequencer (ABI PRISM 3100).
Microarray Analysis Part of the tamoxifen-treated dataset has previously been described (Loi, 2007). Another 77 primary breast cancer samples also treated with tamoxifen monotherapy with corresponding Affymetrix gene expression data was also used for the survival analysis.

For the survival analysis using breast cancer samples which had received no systemic treatment (hereby referred to as the "untreated" dataset), gene expression data was used from datasets described in DESMEDT ET AL., 2007, Clin Cancer Res., 13, 3207-14; WANG ET AL., 2005 and VAN DE VIJVER ET AL., 2002.

The inventors used the normalized data (log 2 intensity in single-channel platforms or log 2 ratio in dual-channel platforms) as published by the original studies. Hybridization probes were mapped to Entrez GeneID. When multiple probes were mapped to the same GeneID, the one with the highest variance in a particular dataset was selected to represent the GeneID.

Data analyses between performed using BRB ArrayTools version 3.5 developed by Dr. Richard Simon and Amy Peng Lam (http://linus.nci.nih.gov/BRB-ArrayTools.html). Differential gene expression between PIK3CA mutation carriers versus non-mutation carriers was performed using the "class comparison" tool. A two sample t– test was used at a significance value of 0.001 and statistical significance of the gene expression profiles between the classes was tested by 1000 permutations of the class labels. For this analysis, of the 173 sequenced for PIK3CA mutations, 161 had corresponding microarray data. Only those samples with exon 20 mutations were used in the class comparison analysis.

The inventors have developed an index called the PIK3CA index that could measure the similarity between the expression profile of any given tumour sample and the PI3K/AKT pathway activation by breast cancers with a PIK3CA mutation. The signature score is the sum of the expression of the genes up-regulated in the mutated tumours minus the sum of the expression of the genes up-regulated in the wild type tumours.
PIK3CA index:

$$\sum_{i \in P} x_i - \sum_{j \in N} x_j$$

where P is the set of genes up-regulated in the mutated tumours and N is the set of genes up-regulated in the wild type tumours.

The weight of the genes was either +1 or −1 depending on their association with PIK3CA mutation status. As a result, the index was not optimized to specifically identify mutation positive samples. Advantageously, no clinical outcome data was used to identify the genes used in the PIK3CA index hence the inventors were able to use the tamoxifen-treated dataset for the survival analyses.
Interaction Networks and Functional Analysis Gene oncology and gene interaction analyses were carried out using Ingenuity Pathways Analysis (IPA) version 3.0 (http://www.ingenuity.com). The gene lists containing the Affymetrix probe, as well as the fold change was inputted into IPA and mapped to the corresponding gene object in the database. These focus genes were then used to generate the networks based on the curated list of molecular interactions in the IPA database. Significance of enrichment is determined by a right-tailed Fisher's exact test, using a list of all the genes on the array as a reference set.
Statistical Analysis Statistical analysis was performed using the SPSS statistical software package (SPSS Inc. Chicago, Ill.) version 13.0. The chi-square test was used to evaluate for possible associations between mutation status and the various clinico-pathological factors. In the univariate and multivariate Cox regression, the histologic grade (grade 1 and. 2 vs. 3), tumour size (≤2 cm vs. >2 cm), nodal status (positive vs. negative) and age (≤50 vs. >50 yrs) were treated as binary variables. The PIK3CA gene signature was treated as a continuous variable. Survival outcomes were also estimated with the Kaplan-Meier method and compared using the log-rank statistic. The PIK3CA gene signature was dichotomized to form two groups for the illustration by Kaplan-Meier survival curves using a cut-off at 66:33% as survival of PIK3CA-GS highest two tertiles of dataset were similar. The group with the higher and lower expression of the PIK3CA-GS is referred to as "mt-like" and "wt-like" respectively.

Breast cancer molecular subgroups were defined using a previously reported method of WIRAPATI ET AL, 2008, Breast cancer cell, 10, R65. The gene expression grade index (GGI) was used as a quantification of the expression of proliferation genes (SOTRIOU ET AL, 2006). For ER+ BC subtypes, proliferation expression was used to classify tumours representing the luminal-A and -B molecular subgroups described by PEROU ET AL., 2000, into luminal low-risk and luminal high-risk subgroups respectively (Loi, 2007).

Results

Frequency and Location of Mutations

Mutational analysis of the PIK3CA gene was performed in 173 primary ER+BCs. A total of 46 mutations were found (26%). The majority (71%) of these mutations were located on exon 20. One sample had mutations in both exon 9 and 20. Twenty-nine (91%) of mutations on exon 20 were H1047R substitutions, its high frequency consistent with previous reports (Table 1). Five AKT1 mutations were found in the 131 samples that were able to be tested (3.8%). All 5 mutations were E17K substitutions, were found in PIK3CA wild type samples.

Mutations and Correlation with Clinico-Pathological Features

Figure 2:
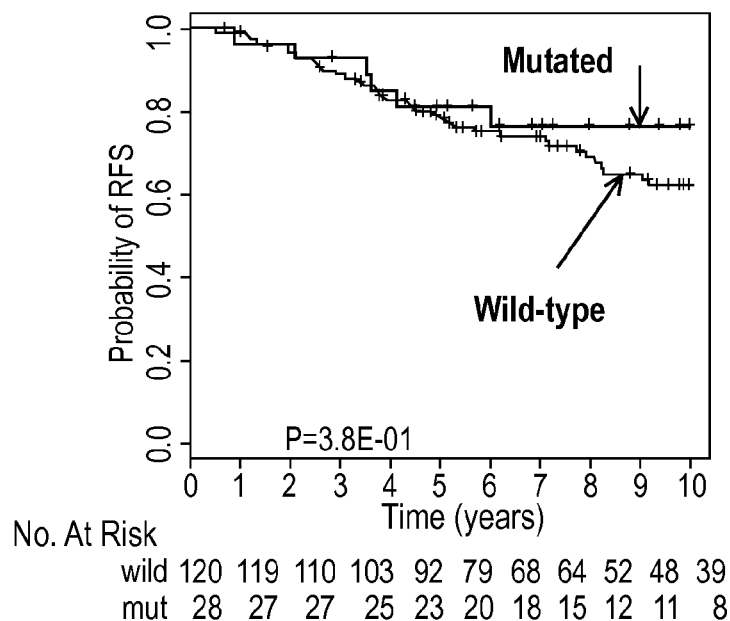

There were no significant correlations between PIK3CA mutations and other important clinico-pathologic features, except a borderline association with tumour size (p=0.057) (Table 1). Similarly, AKT1 mutations were not associated with any clinical factors, though the small numbers make this result difficult to interpret. Kaplan-Meier analysis revealed that mutations of PIK3CA (FIG. 2), AKT1 or both were not significantly correlated with prognosis compared with those tumours without a mutation. PIK3CA exon 9 and 20 mutations were examined combined and separately and results were similar. Univariate survival analysis confirmed no significant correlation between both mutations and prognosis. There was no correlation between either mutation and gene expression grade (GGI) values, suggesting that these mutations are not associated with a particular ER+ molecular subtype. There was no significant association with PIK3CA mutation and ERBB2 or PTEN over expression (p=0.4 and 0.1 respectively).

Microarray Analysis

The lack of correlation of PIK3CA mutations with prognosis with other studies may be due to the unique features of this patient dataset (all ER+ tumours), or that PIK3CA mutations may predict favourably for tamoxifen treatment. Another possibility is that PIK3CA mutations alone are not prognostic in breast cancer but may need to interact with other genetic changes in cancer cells to affect prognosis or other properties of the cancer cells. The corresponding gene expression data was therefore examined with the aim to gain further insight into the biology of activation of the PI3K/AKT pathway through PIK3CA mutations in ER+BC.

PIK3CA Mutation-Positive Associated Differential Gene Expression Signature and Interaction Networks Firstly, those breast cancers harboring PIK3CA exon 20 mutations with available transcriptional profiles (n=28) were compared to wild type samples (n=120). Using a supervised analysis, 81 probe sets were found to be significantly differentially expressed at the nominated t-test level (see Table 2a or the refined tables 2b and Table 4; the genes of Tables 2b and of table 4 are the most suitable genes selected from the Table 2a). The statistical significance of the class label permutation was significant at a p value of 0.03, confirming that the gene expression profiles were significantly different between classes. Results were similar if all mutation samples (exon 9 and 20) were used.

The inventors then performed another statistical analysis by combining the extent of up- or down-regulation (>1.3) and the statistical significance (p<0.05) of a selected gene in mutated cells (Table 5) and further deduce a most preferred signature (Table 6 representing the genes present in both Tables 4 and 5).

The molecular interactions of these differentially expressed genes were examined using Ingenuity Pathways Analysis (IPA). According to Ingenuity Pathways Analysis (IPA), the top canonical pathway was insulin receptor signalling (p=0.002) and the top function was protein synthesis (p=0.0005)

Overall, these data were consistent with the notion that the PI3K pathway is activated by PIK3CA mutations and PIK3CA mutations in breast cancer are associated with a distinct molecular profile.

Activation of the PI3K/Akt Pathway Due to PIK3Ca Mutations Predicts Outcome of ER+Bc Treated with Adjuvant Tamoxifen.

As the molecular profile of the breast cancer samples with a PIK3CA mutation seemed to represent activation of the PI3K/AKT pathway, the inventors went on to create an index using the differentially expressed genes that would be able to quantify the extent of activation of the pathway in a given tumour sample. In this way, the inventors were able to encapsulate clinically relevant activation of this pathway through other mechanisms as well as PIK3CA mutations.

The inventors further found the gene signature of the differentially expressed genes corresponding to mutated PIK3CA and/or AKT in (PIK3CA and/or AKT) wt patients and conclude that the mutated signature they evidenced represents a more physiological read out than the qualitative identification of a mutation in PIK3CA and/or AKT gene(s).

Firstly, the inventors looked at correlation between the PIK3CA mutated signature and subtypes of cancers.

Figure 1:
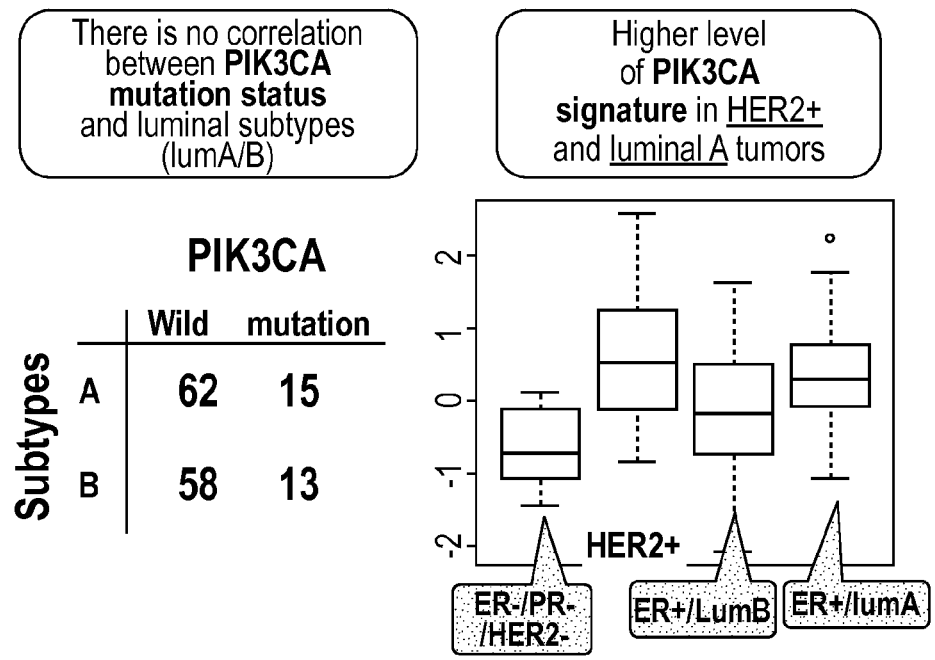

The inventors found no correlation with luminal status of ER+ Breast cancers (FIG. 1).

The inventors found a positive correlation between Her2 positive status and PIK3CA mutated signature (FIG. 1).

Figure 3:
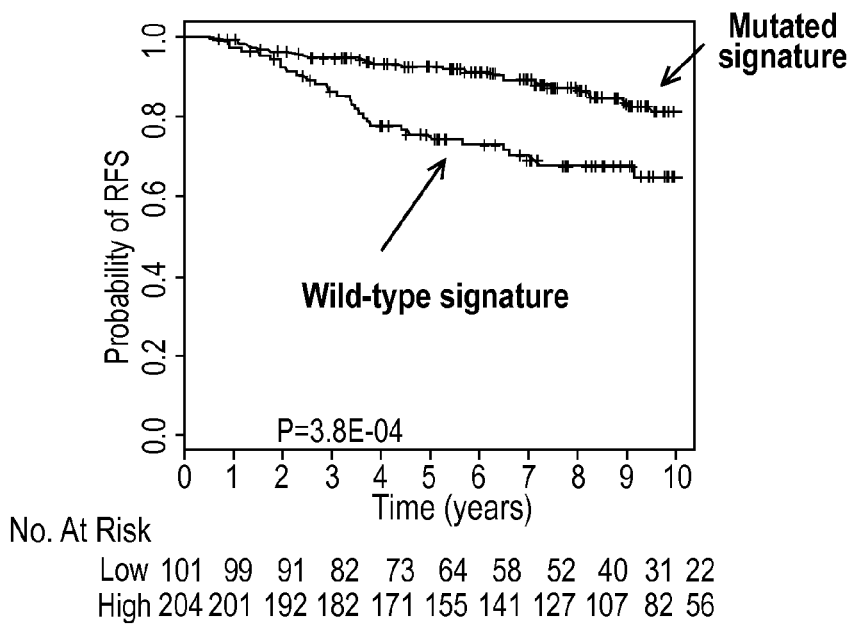
FIG. 3 shows surprisingly that higher expression levels of the PIK3CA signature were associated with statistically better clinical outcome when tamoxifen only treated patient were considered.
Figure 4:
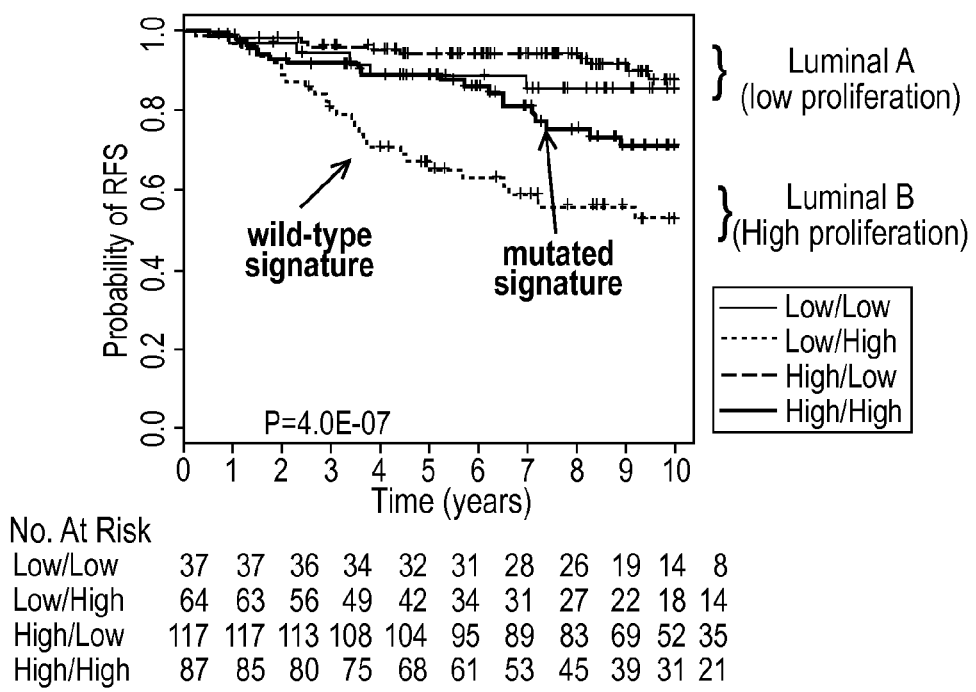
FIG. 4 shows the association between the expression levels of the PIK3CA signature and clinical outcome was better evidenced within the highly proliferative high risk luminal B tumours. Tumours with higher expression levels of the signature benefit better from tamoxifen than those with lower expression levels.

The inventors looked at prognostic ability of PIK3CA index in the dataset of ER+, (HER2-negative) tamoxifen-treated patients. Surprisingly, an increasing expression level of index was associated with a significantly better outcome in these patients (log rank p value: 0.004—FIG. 3). These results were similar in the 405 available patient samples which had not received any systemic treatment (p value: 0.04—FIG. 5). The inventors then went on to look at the relevance of PI3K/AKT activation in the 2 molecular subtypes of ER+BC. Interestingly, in the tamoxifen-treated group, the PIK3CA index was able to separate the luminal-B, but not the luminal-A group of breast cancers into two prognostically distinct groups (p=0.02; FIG. 6). This phenomenon was also observed in the untreated dataset (FIG. 4). However, it noteworthy that in the tamoxifen dataset, the outcome of the luminal-B group treated with tamoxifen with high expression of the PIK3CA index (FIG. 6) seemed to nearly approximate the survival curves of the luminal-A tumours for the first 5 years, suggesting that tamoxifen may, in fact, have a beneficial effect on outcome in this subgroup. Overall, these data suggest that the high expression of the PIK3CA mutation index and hence increased activation of the PI3K/AKT pathway through PIK3CA mutations may predict favourably for tamoxifen treatment in the luminal-B, highly proliferative ER+BCs.

Univariate and multivariate analyses confirmed that the PIK3CA index was able to provide independent prognostic information the tamoxifen dataset (Table 3)

The inventors further looked at the response of Her2 positive BC patients treated with tamoxifen and observed that the Her2 positive BC patients having the mutated PIK3CA signature responded better to tamoxifen than the other Her2 positive patients.

The inventors conclude that anti oestrogen treatments may be useful for Her2 positive BC patients having the mutated PIK3CA signature.

The overall incidence of PIK3CA mutations found in this current study is within the range of the four other reported large studies on PIK3CA mutations in breast cancer, even though the analysis of the PIK3CA gene in this study was restricted to exons 9 and 20 only. In contrast to other studies, the majority of mutations found were located on exon 20. This is most likely, because almost all of the breast cancers in this data set were invasive ductal carcinomas, consistent with previous observations that exon 9 mutations are more common in invasive lobular carcinoma. The incidence of PIK3CA mutations observed to date makes it one of the commonest genetic alterations in breast cancer.

This study, similar to others, did not find a particular association of PIK3CA mutations with breast cancer clinicopathological characteristics (Table 1). The only consistent finding thus far has been the association between PIK3CA mutations and a positive ER status.

The inventors report here for the first time the incidence and clinical outcome of AKT1 PHD mutations in ER+BC treated with adjuvant tamoxifen monotherapy. AKT1 PHD mutations have been reported to activate the PI3K/AKT pathway. The incidence here was lower than previously reported (3.8% vs. 8%), which makes the results from further analyses difficult to interpret. Interestingly, all AKT1 mutations occurred in PIK3CA wild type samples. However, neither PIK3CA and/or AKT1 PHD mutations per se were associated with prognosis in our ER+BC dataset. These data does not support a recent study which reported that in breast cancer, PIK3CA mutations located on exon 9 conveyed a worse prognosis that those located on exon 20, though the incidence of exon 9 mutations here was less. Given the conflicting data in the literature and the low incidence of AKT1 mutations, it seems it may be impossible to use PIK3CA and AKT1 mutation status alone to predict prognosis and treatment response. AKT1 PHD mutations may even predict for a favourable prognosis given that cell line and animal models suggest that unlike AKT2, AKT1 does not influence invasion and metastases.

However, the PI3K/AKT pathway is complex, impacting on multiple areas of cell physiology, hence activation of the pathway by different mechanisms is likely to trigger different cellular functions. Using the corresponding gene expression data, the inventors were able to identify a molecular profile from PIK3CA mutation positive breast cancers. The inventors then used the 81 genes to form an index that could quantify the level of PI3K/AKT pathway activation of a given tumour similar to that triggered by a PIK3CA mutation. Interestingly, the inventors found that in ER+BC, high expression of the index, or activation of the PI3K/AKT pathway seemed to predict for a better outcome and also a beneficial effect from tamoxifen treatment. This finding was most impressive in the luminal-B subgroup, which normally has a poor prognosis compared with the luminal-A subgroup. The index was relevant to tumour samples that were negative for PIK3CA mutations, implying that those tumours with high expression of the PIK3CA signature had clinically relevant PI3K/AKT pathway deregulation through some other mechanism. The PIK3CA signature could therefore be a better indicator of pathway dysfunction than mutation status per se.

Given the multiple levels of molecular interactions in the PI3K/AKT pathway, it is not inconceivable that different activators of the pathway will be associated with different transcriptional profiles and clinical outcomes.

In cell lines, PIK3CA mutant lines including MCF7 and T47D, were found to be more sensitive to tamoxifen than PIK3CA normal lines. These results may be extremely significant for the luminal-B subtype as it could identify which tumours may benefit from endocrine therapy and which tumours will require other treatments to alter its poor prognosis. It will also be important in the future to determine whether the PIK3CA gene set can predict response to PI3K inhibitors.

The inventors report that PIK3CA mutations and for the first time, AKT1 mutations do not correlate with prognosis in a large cohort of ER+BCs treated with adjuvant tamoxifen monotherapy. The inventors disclose a gene signature that identifies those ER+BCs with clinically relevant activation of the PI3K/AKT pathway, and identify those breast cancers that respond favourably to tamoxifen. These findings are particularly significant for the luminal-B ER+ subgroup and may provide useful stratification in future clinical trials evaluating endocrine therapy in ER+BC.

Furthermore, the inventors compared the outcome of breast cancer patients having the wild-type signature with the outcome of patients having the mutated signature (according to the present invention), when treated with a PI3kinase (pathway) inhibitor, being 10 mg per day of Everolimus (Afinitor® or RAD001 from Novartis) (an mTOR inhibitor) taken orally. The inventors further selected patients having a ER+ breast cancer and patients having a Her2+ breast cancer and compared the effect of Everolimus in function of the wild-type or mutated signature (according to the present invention).

Other inhibitors of the PI3K/Akt/mTOR pathway, such as WYE-354, CCI-779 (from wyeth), Temsirolimus, GSK1059615, Deforolimus, KU-0063794, PI-103 and NVP-BEZ235 can be used as well.

TABLE 1

(A)

| Exon | Nucleotide change | Amino acid change | Number of cases (%) |
| --- | --- | --- | --- |
| 20 | A3140G | H1047R | 29 (91%) |
| 20 | A3150T | H1047L | 3 (9%) |
| 9 | G1633A | E545K | 7 (50%) |
| 9 | G1624A | E542K | 6 (43%) |
| 9 | G1634A | E545G | 1 (7%) |
| Total | | | 46 (100%) |

TABLE 1-continued (B)

| Variable | Total cases (n = 173) | Mutated (n = 45) | Normal (n = 127) | P value |
|---|---|---|---|---|
| Age | | | | 0.3 |
| ≤50 yrs | 14 | 2 (36%) | 12 (66%) | |
| >50 yrs | 157 | 43 (27%) | 114 (73%) | |
| Tumour size | | | | 0.057 |
| T1 ≤ 2 cm | 76 | 15 (20%) | 61 (80%) | |
| T2 > 2 cm | 95 | 30 (32%) | 65 (78%) | |
| Histologic Grade | | | | 0.5 |
| Grade 1 | 28 | 7 (25%) | 21 (75%) | |
| Grade 2 | 80 | 23 (26%) | 57 (74%) | |
| Grade 3 | 32 | 7 (22%) | 25 (78%) | |
| Nodal status | | | | 0.5 |
| Node positive | 87 | 23 (26%) | 64 (74%) | |
| Node negative | 83 | 21 (25%) | 62 (75%) | |
| ER+ molecular subtype * | | | | |
| Luminal A (GGI low) | 87 | 25 (29%) | 62 (71%) | 0.3 |
| Luminal B (GGI hi) | 79 | 17 (22%) | 62 (78%) | |

Note
1) all 173 BC samples were ER+;
2) for some samples, values were missing;
3) for those samples whose gene expression data (n = 161) were available, 41 samples had PIK3CA mutations.
* see reference LOI ET AL., 2007.

TABLE 2a

| Rank | Parametric p-value | FDR | Ratio > 1 = up-regulated in WT | Affymetrix Probe set | Gene symbol |
|---|---|---|---|---|---|
| 1 | 8.00E−07 | 0.02 | 1.111 | 203012_x_at | RPL23A |
| 2 | 2.54E−05 | 0.14 | 1.111 | 208825_x_at | RPL23A |
| 3 | 3.13E−05 | 0.14 | 1.111 | 222327_x_at | OR7E156P |
| 4 | 3.97E−05 | 0.14 | 1.375 | 219138_at | RPL14 |
| 5 | 4.18E−05 | 0.14 | 0.524 | 206994_at | CST4 |
| 6 | 5.25E−05 | 0.14 | 0.2 | 206378_at | SCGB2A2 |
| 7 | 6.34E−05 | 0.14 | 1.375 | 208229_at | FGFR2 |
| 8 | 7.94E−05 | 0.14 | 0.75 | 212377_s_at | NOTCH2 |
| 9 | 8.86E−05 | 0.14 | 1.8 | 204992_s_at | PFN2 |
| 10 | 8.88E−05 | 0.14 | 1.375 | 211406_at | IER3IP1 |
| 11 | 9.49E−05 | 0.14 | 1.111 | 206447_at | ELA2A |
| 12 | 9.50E−05 | 0.14 | 1.111 | 202002_at | ACAA2 |
| 13 | 9.76E−05 | 0.14 | 1.375 | 211212_s_at | ORC5L |
| 14 | 9.78E−05 | 0.14 | 1.222 | 218238_at | GTPBP4 |
| 15 | 0.0001 | 0.14 | 1.222 | 209535_s_at | |
| 16 | 0.0001 | 0.16 | 1.833 | 202431_s_at | MYC |
| 17 | 0.0001 | 0.16 | 0.667 | 212415_at | SEPT6 |
| 18 | 0.0001 | 0.16 | 1.375 | 202300_at | HBXIP |
| 19 | 0.0001 | 0.16 | 1.222 | 203551_s_at | COX11 |
| 20 | 0.0001 | 0.16 | 0.692 | 202743_at | PIK3R3 |
| 21 | 0.0001 | 0.16 | 0.75 | 221704_s_at | VPS37B |
| 22 | 0.0001 | 0.17 | 0.733 | 213109_at | TNIK |
| 23 | 0.0002 | 0.18 | 1.375 | 202028_s_at | |
| 24 | 0.0002 | 0.18 | 1.625 | 214051_at | MGC39900 |
| 25 | 0.0002 | 0.18 | 0.833 | 202215_s_at | NFYC |
| 26 | 0.0002 | 0.19 | 0.75 | 202443_x_at | NOTCH2 |
| 27 | 0.0002 | 0.19 | 1.111 | 220549_at | FSBP /// RAD54B |
| 28 | 0.0002 | 0.19 | 0.538 | 217771_at | GOLPH2 |
| 29 | 0.0002 | 0.19 | 0.909 | 207801_s_at | RNF10 |
| 30 | 0.0002 | 0.19 | 0.692 | 201288_at | ARHGDIB |
| 31 | 0.0002 | 0.19 | 0.769 | 215894_at | PTGDR |
| 32 | 0.0002 | 0.19 | 0.692 | 217787_s_at | GALNT2 |
| 33 | 0.0003 | 0.19 | 1.375 | 209046_s_at | GABARAPL2 |
| 34 | 0.0003 | 0.19 | 1.714 | 209185_s_at | IRS2 |
| 35 | 0.0003 | 0.19 | 0.692 | 203128_at | SPTLC2 |
| 36 | 0.0003 | 0.19 | 1.111 | 211677_x_at | IGSF4B |
| 37 | 0.0003 | 0.19 | 0.212 | 206799_at | SCGB1D2 |
| 38 | 0.0003 | 0.19 | 1.333 | 221586_s_at | E2F5 |
| 39 | 0.0003 | 0.19 | 0.909 | 215339_at | NKTR |
| 40 | 0.0003 | 0.19 | 1.25 | 222151_s_at | Cep63 |
| 41 | 0.0003 | 0.19 | 1.375 | 216609_at | TXN |
| 42 | 0.0003 | 0.19 | 1.111 | 219590_x_at | DPH5 |
| 43 | 0.0004 | 0.20 | 1.111 | 221915_s_at | RANBP1 |
| 44 | 0.0004 | 0.20 | 0.833 | 200058_s_at | ASCC3L1 |
| 45 | 0.0004 | 0.20 | 0.833 | 218815_s_at | TMEM51 |

TABLE 2a-continued

| Rank | Parametric p-value | FDR | Ratio > 1 = up-regulated in WT | Affymetrix Probe set | Gene symbol |
|---|---|---|---|---|---|
| 46 | 0.0004 | 0.20 | 0.562 | 211828_s_at | TNIK |
| 47 | 0.0004 | 0.20 | 1.111 | 218023_s_at | FAM53C |
| 48 | 0.0004 | 0.20 | 1.222 | 214508_x_at | CREM |
| 49 | 0.0004 | 0.20 | 0.692 | 220066_at | CARD15 |
| 50 | 0.0004 | 0.20 | 0.909 | 221205_at | |
| 51 | 0.0004 | 0.20 | 1.375 | 201171_at | ATP6V0E |
| 52 | 0.0004 | 0.20 | 1.111 | 212270_x_at | RPL17 |
| 53 | 0.0005 | 0.20 | 0.833 | 207082_at | CSF1 |
| 54 | 0.0005 | 0.20 | 0.833 | 216050_at | |
| 55 | 0.0005 | 0.20 | 1.222 | 218239_s_at | GTPBP4 |
| 56 | 0.0005 | 0.22 | 1.222 | 214553_s_at | ARPP-19 |
| 57 | 0.0006 | 0.23 | 1.375 | 213133_s_at | GCSH |
| 58 | 0.0006 | 0.23 | 0.833 | 200999_s_at | CKAP4 |
| 59 | 0.0006 | 0.23 | 0.667 | 208502_s_at | PITX1 |
| 60 | 0.0006 | 0.23 | 1.222 | 203565_s_at | MNAT1 |
| 61 | 0.0006 | 0.23 | 0.818 | 212756_s_at | UBR2 |
| 62 | 0.0006 | 0.23 | 0.833 | 210369_at | SWAP70 |
| 63 | 0.0007 | 0.24 | 0.833 | 219247_s_at | ZDHHC14 |
| 64 | 0.0007 | 0.25 | 0.818 | 203250_at | RBM16 |
| 65 | 0.0007 | 0.25 | 1.375 | 202481_at | DHRS3 |
| 66 | 0.0008 | 0.25 | 1.25 | 212519_at | UBE2E1 |
| 67 | 0.0008 | 0.25 | 1.111 | 202810_at | DRG1 |
| 68 | 0.0008 | 0.25 | 1.111 | 211952_at | RANBP5 |
| 69 | 0.0008 | 0.25 | 1.375 | 204807_at | TMEM5 |
| 70 | 0.0008 | 0.25 | 0.909 | 222115_x_at | N-PAC |
| 71 | 0.0008 | 0.25 | 1.222 | 205811_at | POLG2 |
| 72 | 0.0008 | 0.25 | 0.75 | 221041_s_at | SLC17A5 |
| 73 | 0.0008 | 0.25 | 0.833 | 207407_x_at | CYP4A11 |
| 74 | 0.0008 | 0.25 | 1 | 208834_x_at | RPL23A |
| 75 | 0.0008 | 0.25 | 1.111 | 215741_x_at | AKAP8L |
| 76 | 0.0009 | 0.25 | 0.75 | 200660_at | S100A11 |
| 77 | 0.0009 | 0.25 | 1.25 | 218411_s_at | MBIP |
| 78 | 0.0009 | 0.25 | 1.222 | 210779_x_at | SIP1 |
| 79 | 0.0009 | 0.25 | 1.111 | 212500_at | C10orf22 |
| 80 | 0.0009 | 0.25 | 0.833 | 208876_s_at | PAK2 |
| 81 | 0.0009 | 0.25 | 1.222 | 220762_s_at | GNB1L |

WT: wild type; FDR: false discovery rate

TABLE 2b

| Probe Set ID | Gene Symbol | Gene Title | Entrez Gene ID |
|---|---|---|---|
| 202002_at | ACAA2 | acetyl-Coenzyme A acyltransferase 2 | 10449 |
| 215741_x_at | AKAP8L | A kinase (PRKA) anchor protein 8-like | 26993 |
| 201288_at | ARHGDIB | Rho GDP dissociation inhibitor (GDI) beta | 397 |
| 214553_s_at | ARPP-19 | cyclic AMP phosphoprotein, 19 kD | 10776 |
| 200058_s_at | ASCC3L1 | activating signal cointegrator 1 complex subunit 3-like 1 | 23020 |
| 201171_at | ATP6V0E1 | ATPase, H+ transporting, lysosomal 9 kDa, V0 subunit e1 | 8992 |
| 219242_at | CEP63 | centrosomal protein 63 kDa | 80254 |
| 200998_s_at | CKAP4 | cytoskeleton-associated protein 4 | 10970 |
| 203551_s_at | COX11 | COX11 homolog, cytochrome c oxidase assembly protein (yeast) | 1353 |
| 207630_s_at | CREM | cAMP responsive element modulator | 1390 |
| 207082_at | CSF1 | colony stimulating factor 1 (macrophage) | 1435 |
| 206994_at | CST4 | cystatin S | 1472 |
| 207407_x_at | CYP4A11 | cytochrome P450, family 4, subfamily A, polypeptide 11 | 1579 |
| 202481_at | DHRS3 | dehydrogenase/reductase (SDR family) member 3 | 9249 |
| 219590_x_at | DPH5 | DPH5 homolog (S. cerevisiae) | 51611 |
| 202810_at | DRG1 | developmentally regulated GTP binding protein 1 | 4733 |
| 221586_s_at | E2F5 | E2F transcription factor 5, p130-binding | 1875 |
| 206447_at | ELA2A | elastase 2A | 63036 |
| 218023_s_at | FAM53C | family with sequence similarity 53, member C | 51307 |
| 208229_at | FGFR2 | fibroblast growth factor receptor 2 | 2263 |
| 209046_s_at | GABARAPL2 | GABA(A) receptor-associated protein-like 2 | 11345 |
| 217787_s_at | GALNT2 | UDP-N-acetyl-alpha-D-galactosamine:polypeptide N-acetylgalactosaminyltransferase 2 (GalNAc-T2) | 2590 |
| 213133_s_at | GCSH///LOC730107 | glycine cleavage system protein H (aminomethyl carrier)///similar to Glycine cleavage system H protein, mitochondrial | 2653///730107 |
| 220762_s_at | GNB1L | guanine nucleotide binding protein (G protein), beta polypeptide 1-like | 54584 |
| 218238_at | GTPBP4 | GTP binding protein 4 | 23560 |
| 211406_at | IER3IP1 | immediate early response 3 interacting protein 1 | 51124 |
| 209184_s_at | IRS2 | insulin receptor substrate 2 | 8660 |
| 218411_s_at | MBIP | MAP3K12 binding inhibitory protein 1 | 51562 |
| 214051_at | MGC39900///TMSL8 | thymosin beta15b///thymosin-like 8 | 11013///286527 |

TABLE 2b-continued

| Probe Set ID | Gene Symbol | Gene Title | Entrez Gene ID |
|---|---|---|---|
| 203565_s_at | MNAT1 | menage a trois homolog 1, cyclin H assembly factor (*Xenopus laevis*) | 4331 |
| 202431_s_at | MYC | v-myc myelocytomatosis viral oncogene homolog (avian) | 4609 |
| 202215_s_at | NFYC | nuclear transcription factor Y, gamma | 4802 |
| 215339_at | NKTR | natural killer-tumor recognition sequence | 4820 |
| 202443_x_at | NOTCH2 | Notch homolog 2 (Drosophila) | 4853 |
| 222115_x_at | N-PAC | cytokine-like nuclear factor n-pac | 84656 |
| 222327_x_at | OR7E156P | olfactory receptor, family 7, subfamily E, member 156 pseudogene | 283491 |
| 211212_s_at | ORC5L | origin recognition complex, subunit 5-like (yeast) | 5001 |
| 208876_s_at | PAK2 | p21 protein (Cdc42/Rac)-activated kinase 2 | 5062 |
| 204992_s_at | PFN2 | profilin 2 | 5217 |
| 202743_at | PIK3R3 | phosphoinositide-3-kinase, regulatory subunit 3 (gamma) | 8503 |
| 208502_s_at | PITX1 | paired-like homeodomain 1 | 5307 |
| 205811_at | POLG2 | polymerase (DNA directed), gamma 2, accessory subunit | 11232 |
| 215894_at | PTGDR | prostaglandin D2 receptor (DP) | 5729 |
| 221915_s_at | RANBP1 | RAN binding protein 1 | 5902 |
| 203250_at | RBM16 | RNA binding motif protein 16 | 22828 |
| 207801_s_at | RNF10 | ring finger protein 10 | 9921 |
| 219138_at | RPL14 | ribosomal protein L14 | 9045 |
| 212537_x_at | RPL17 | ribosomal protein L17 | 6139 |
| 203012_x_at | RPL23A | ribosomal protein L23a | 6147 |
| 200660_at | S100A11 | S100 calcium binding protein A11 | 6282 |
| 206799_at | SCGB1D2 | secretoglobin, family 1D, member 2 | 10647 |
| 206378_at | SCGB2A2 | secretoglobin, family 2A, member 2 | 4250 |
| 210779_x_at | SIP1 | survival of motor neuron protein interacting protein 1 | 8487 |
| 221041_s_at | SLC17A5 | solute carrier family 17 (anion/sugar transporter), member 5 | 26503 |
| 203127_s_at | SPTLC2 | serine palmitoyltransferase, long chain base subunit 2 | 9517 |
| 210369_at | SWAP70 | SWAP-70 protein | 23075 |
| 204807_at | TMEM5 | transmembrane protein 5 | 10329 |
| 218815_s_at | TMEM51 | transmembrane protein 51 | 55092 |
| 211828_s_at | TNIK | TRAF2 and NCK interacting kinase | 23043 |
| 216609_at | TXN | Thioredoxin | 7295 |
| 212519_at | UBE2E1 | ubiquitin-conjugating enzyme E2E 1 (UBC4/5 homolog, yeast) | 7324 |
| 212756_s_at | UBR2 | ubiquitin protein ligase E3 component n-recognin 2 | 23304 |
| 221704_s_at | VPS37B | ubiquitin protien sorting 37 homolog B (*S. cerevisiae*) | 79720 |
| 219247_s_at | ZDHHC14 | zinc finger, DHHC-type containing 14 | 79683 |

TABLE 3

(A)

| Factor | Univariate HR | P value | Multivariate HR* | P value |
|---|---|---|---|---|
| Age | 1.8 (0.6-5.7) | 0.3 | | |
| Tumor size | 2.9 (1.6-5.0) | 0.0002 | 3.2 (1.3-8.7) | 0.01 |
| Nodal status | 2.1 (1.2-3.5) | 0.0004 | 0.9 (0.4-2.3) | 0.9 |
| Histologic grade^ | 1.8 (1.1-2.6) | 0.005 | | |
| PIK3CA mutation | 0.6 (0.3-1.4) | 0.26 | | |
| PIK3CA index | 0.4 (0.3-0.7) | 0.01 | 0.5 (0.3-0.8) | 0.01 |
| Luminal B vs A subtype# | 2.2 (1.6-3.0) | 0.0000004 | 2.2 (1.3-3.7) | 0.004 |

Total patient samples: 305

TABLE 3-continued (B)

| Factor | Univariate HR | P value | Multivariate HR |
|---|---|---|---|
| Age | 0.9 (0.6-1.6) | 0.8 | |
| Tumor size | 1.7 (1.1-2.8) | 0.03 | |
| Nodal status | 1.0 (0.4-2.7) | 0.1 | |
| Histologic grade^ | 4.2 (2.2-7.8) | 0.00000007 | |
| PIK3CA index | 0.7 (0.5-0.9) | 0.03 | |
| Luminal B vs A subtype# | 3.0 (1.9-4.6) | 0.0000006 | |

Total patient samples: 425
*Only those factors significant in the Univariate analysis were used in the multivariate model.
^histologic grade was not used in the multivariate model has highly correlated to the gene expression grade index (GGI)
as defined by the GGI (see LOI ET AL; 2007)
HR: hazard ratio

TABLE 4

Preferred genes associated with PIK3CA mutation

| Probe Set ID | Gene Symbol | Gene Title | Entrez Gene ID |
|---|---|---|---|
| 212500_at | ADO | 2-aminoethanethiol (cysteamine) dioxygenase | 84890 |
| 201288_at | ARHGDIB | Rho GDP dissociation inhibitor (GDI) beta | 397 |
| 214553_s_at | ARPP-19 | cyclic AMP phosphoprotein, 19 kD | 10776 |
| 200058_s_at | ASCC3L1 | activating signal cointegrator 1 complex subunit 3-like 1 | 23020 |
| 222151_s_at | CEP63 | centrosomal protein 63 kDa | 80254 |
| 200999_s_at | CKAP4 | cytoskeleton-associated protein 4 | 10970 |
| 203551_s_at | COX11 | COX11 homolog, cytochrome c oxidase assembly protein (yeast) | 1353 |
| 214508_x_at | CREM | cAMP responsive element modulator | 1390 |

TABLE 4-continued

Preferred genes associated with PIK3CA mutation

| Probe Set ID | Gene Symbol | Gene Title | Entrez Gene ID |
|---|---|---|---|
| 202481_at | DHRS3 | dehydrogenase/reductase (SDR family) member 3 | 9249 |
| 219590_x_at | DPH5 | DPH5 homolog (S. cerevisiae) | 51611 |
| 221586_s_at | E2F5 | E2F transcription factor 5, p130-binding | 1875 |
| 218023_s_at | FAM53C | family with sequence similarity 53, member C | 51307 |
| 217787_s_at | GALNT2 | UDP-N-acetyl-alpha-D-galactosamine:polypeptide N-acetylgalactosaminyltransferase 2 (GalNAc-T2) | 2590 |
| 213133_s_at | GCSH/// LOC730107 | glycine cleavage system protein H (aminomethyl carrier)/// similar to Glycine cleavage system H protein, mitochondrial | 2653///730107 |
| 217771_at | GOLM1 | golgi membrane protein 1 | 51280 |
| 218238_at | GTPBP4 | GTP binding protein 4 | 23560 |
| 202300_at | HBXIP | hepatitis B virus x interacting protein | 10542 |
| 218411_s_at | MBIP | MAP3K12 binding inhibitory protein 1 | 51562 |
| 203565_s_at | MNAT1 | menage a trois homolog 1, cyclin H assembly factor (Xenopus laevis) | 4331 |
| 202431_s_at | MYC | v-myc myelocytomatosis viral oncogene homolog (avian) | 4609 |
| 202215_s_at | NFYC | nuclear transcription factor Y, gamma | 4802 |
| 215339_at | NKTR | natural killer-tumor recognition sequence | 4820 |
| 212377_s_at | NOTCH2 | Notch homolog 2 (Drosophila) | 4853 |
| 222115_x_at | N-PAC | cytokine-like nuclear factor n-pac | 84656 |
| 211212_s_at | ORC5L | origin recognition complex, subunit 5-like (yeast) | 5001 |
| 204992_s_at | PFN2 | profilin 2 | 5217 |
| 202743_at | PIK3R3 | phosphoinositide-3-kinase, regulatory subunit 3 (gamma) | 8503 |
| 203250_at | RBM16 | RNA binding motif protein 16 | 22828 |
| 200660_at | S100A11 | S100 calcium binding protein A11 | 6282 |
| 206378_at | SCGB2A2 | secretoglobin, family 2A, member 2 | 4250 |
| 210779_x_at | SIP1 | survival of motor neuron protein interacting protein 1 | 8487 |
| 203128_at | SPTLC2 | serine palmitoyltransferase, long chain base subunit 2 | 9517 |
| 218815_s_at | TMEM51 | transmembrane protein 51 | 55092 |
| 211828_s_at | TNIK | TRAF2 and NCK interacting kinase | 23043 |
| 212519_at | UBE2E1 | ubiquitin-conjugating enzyme E2E 1 (UBC4/5 homolog, yeast) | 7324 |
| 212756_s_at | UBR2 | ubiquitin protein ligase E3 component n-recognin 2 | 23304 |
| 221704_s_at | VPS37B | vacuolar protein sorting 37 homolog B (S. cerevisiae) | 79720 |
| 219247_s_at | ZDHHC14 | zinc finger, DHHC-type containing 14 | 79683 |

ADO is also mentioned as C10orf22;
GOLM1 is also mentioned as GOLPH2.

TABLE 5

Alternative PIK 3CA gene signature
PIK3CA-GS predictor FC > 1.3 p < 0.05

| rank accord | p value | Fold Change | Probe set | Description | Gene symbol | Entrez Gene ID | Coef-fic | Cytoband |
|---|---|---|---|---|---|---|---|---|
| 370 | 0.01 | -2.16 | 204637_at | glycoprotein hormones, alpha polypeptide | CGA | 1081 | -1 | 6q12-q21 |
| 325 | 0.0045 | -1.91 | 209242_at | paternally expressed 3 | PEG3 | 5178 | -1 | 19q13.4 |
| 248 | 0.0033 | -1.79 | 219109_at | sperm associated antigen 16 | SPAG16 | 79582 | -1 | 2q34 |
| 16 | 0.0001 | -1.78 | 202431_s_at | v-myc myelocytomatosis viral oncogene homolog (avian) | MYC | 4609 | -1 | 8q24.21 |
| 89 | 0.0011 | -1.78 | 203987_at | frizzled homolog 6 (Drosophila) | FZD6 | 8323 | -1 | 8q22.3-q23.1 |
| 354 | 0.0049 | -1.75 | 211548_s_at | hydroxyprostaglandin dehydrogenase 15-(NAD) | HPGD | 3248 | -1 | 4q34-q35 |
| 537 | 0.01 | -1.74 | 203914_x_at | hydroxyprostaglandin dehydrogenase 15-(NAD) | HPGD | 3248 | -1 | 4q34-q35 |
| 9 | 0.0001 | -1.73 | 204992_s_at | profilin 2 | PFN2 | 5217 | -1 | 3q25.1-q25.2 |
| 207 | 0.0027 | -1.71 | 204688_at | sarcoglycan, epsilon | SGCE | 8910 | -1 | 7q21-q22 |
| 582 | 0.01 | -1.70 | 221582_at | histone 3, H2a | HIST3H2A | 92815 | -1 | 1q42.13 |
| 24 | 0.0002 | -1.70 | 214051_at | hypothetical protein MGC39900 | MGC39900 | 286527 | -1 | Xq22.2 |
| 762 | 0.01 | -1.68 | 218730_s_at | osteoglycin (osteoinductive factor, mimecan) | OGN | 4969 | -1 | 9q22 |
| 1206 | 0.02 | -1.66 | 206110_at | histone 1, H3h | HIST1H3H | 3109 | -1 | — |
| 150 | 0.0018 | -1.66 | 202620_s_at | procollagen-lysine, 2-oxogluterate 5-dioxygenase 2 | PLOD2 | 5352 | -1 | 3q23-q24 |
| 34 | 0.0003 | -1.63 | 209185_s_at | insulin receptor substrate 2 | IRS2 | 8660 | -1 | 13q34 |
| 621 | 0.01 | -1.62 | 207156_at | histone 1, H2ag | HIST1H2AG | 8969 | -1 | 6p22.1 |
| 936 | 0.02 | -1.60 | 206070_s_at | EPH receptor A3 | EPHA3 | 2042 | -1 | 3p11.2 |
| 1067 | 0.02 | -1.58 | 205280_at | glycine receptor, beta | GLRB | 2743 | -1 | 4q31.3 |
| 267 | 0.0035 | -1.58 | 202619_s_at | procollagen-lysine, 2-oxogluterate 5-dioxygenase 2 | PLOD2 | 5352 | -1 | 3q23-q24 |
| 82 | 0.0010 | -1.57 | 217963_s_at | nerve growth factor receptor (TNFRSF16) associated protein 1 | NGFRAP1 | 27018 | -1 | Xq22.2 |
| 779 | 0.01 | -1.57 | 203895_at | phospholipase C, beta 4 | PLCB4 | 5332 | -1 | 20p12 |
| 1290 | 0.03 | -1.53 | 203913_s_at | hydroxyprostaglandin dehydrogenase 15-(NAD) | HPGD | 3248 | -1 | 4q34-q35 |
| 183 | 0.0024 | -1.51 | 204566_at | protein phosphatase 1D magnesium-dependent delta isoform | PPM1D | 8493 | -1 | 17q23.2 |
| 201 | 0.0026 | -1.51 | 204939_s_at | phospholamban | PLN | 5350 | -1 | 6q22.1 |

TABLE 5-continued

Alternative PIK 3CA gene signature
PIK3CA-GS predictor FC > 1.3 p < 0.05

| rank accord | p value | Fold Change | Probe set | Description | Gene symbol | Entrez Gene ID | Coef-fic | Cytoband |
|---|---|---|---|---|---|---|---|---|
| 2099 | 0.05 | −1.49 | 218541_s_at | chromosome 8 open reading frame 4 | C8orf4 | 56892 | −1 | 8p11.2 |
| 202 | 0.0026 | −1.49 | 209184_s_at | insulin receptor substrate 2 | IRS2 | 8660 | −1 | 13q34 |
| 1730 | 0.04 | −1.49 | 214469_at | histone 1, H2ae | HIST1H2AE | 3012 | −1 | 6p22.2-p21.1 |
| 1322 | 0.03 | −1.49 | 205279_s_at | glycine receptor, beta | GLRB | 2743 | −1 | 4q31.3 |
| 811 | 0.01 | −1.48 | 201116_s_at | carboxypeptidase E | CPE | 1363 | −1 | 4q32.3 |
| 454 | 0.01 | −1.47 | 204042_at | WAS protein family, member 3 | WASF3 | 10810 | −1 | 13q12 |
| 417 | 0.01 | −1.46 | 201030_x_at | lactate dehydrogenase B | LDHB | 3945 | −1 | 12p12.2-p12.1 |
| 1763 | 0.04 | −1.46 | 202708_s_at | histone 2, H2be | HIST2H2BE | 8349 | −1 | 1q21-q23 |
| 1646 | 0.04 | −1.45 | 218280_x_at | histone 2, H2aa | HIST2H2AA | 8337 | −1 | 1q21.2 |
| 711 | 0.01 | −1.44 | 203608_at | aldehyde dehydrogenase 5 family, member A1 (succinateaemialdehyde dehydrogenase) | ALDH5A1 | 7915 | −1 | 6p22.2-p22.3 |
| 558 | 0.01 | −1.44 | 213564_x_at | lactate dehydrogenase B | LDHB | 3945 | −1 | 12p12.2-p12.1 |
| 1555 | 0.03 | −1.44 | 214290_s_at | histone 2, H2aa | HIST2H2AA | 8337 | −1 | 1q21.2 |
| 1742 | 0.04 | −1.43 | 212154_at | syndecan 2 (heparan sulfate proteoglycan 1, cell surface-associated, fibroglycan) | SDC2 | 6383 | −1 | 8q22-q23 |
| 92 | 0.0011 | −1.43 | 218732_at | Bcl-2 inhibitor of transcription | BIT1 | 51651 | −1 | 17q23.1 |
| 319 | 0.0043 | −1.43 | 211578_s_at | ribosomal protein S6 kinase, 70 kDa, polypeptide 1 | RPS6KB1 | 6198 | −1 | 17q23.1 |
| 1050 | 0.02 | −1.42 | 212859_x_at | metallothionein 1E (functional) | MT1E | 4493 | −1 | 16q13 |
| 103 | 0.0013 | −1.42 | 202630_at | amyloid beta precursor protein (cytoplasmic tail) binding protein 2 | APPBP2 | 10513 | −1 | 17q21-q23 |
| 2084 | 0.05 | −1.42 | 204916_at | receptor (calcitonin) activity modifying protein 1 | RAMP1 | 10267 | −1 | 2q36-q37.1 |
| 250 | 0.0033 | −1.41 | 209526_s_at | hepatoma-derived growth factor, related protein 3 | HDGFRP3 | 50810 | −1 | 15q25.2 |
| 994 | 0.02 | −1.41 | 219312_s_at | zinc finger and BTB domain containing 10 | ZBTB10 | 65986 | −1 | 8q13-q21.1 |
| 1472 | 0.03 | −1.41 | 206825_at | oxytocin receptor | OXTR | 5021 | −1 | 3p25 |
| 1128 | 0.02 | −1.41 | 212589_at | Sterol carrier protein 2 | SCP2 | 22800 | −1 | 11p15.2 |
| 1172 | 0.02 | −1.41 | 213793_s_at | homer homolog 1 (Drosophila) | HOMER1 | 9456 | −1 | 5q14.2 |
| 38 | 0.0004 | −1.41 | 221586_s_at | E2F transcription factor 5, p130-binding | E2F5 | 1875 | −1 | 8q21.2 |
| 533 | 0.01 | −1.41 | 213562_s_at | squalene epoxidase | SQLE | 6713 | −1 | 8q24.1 |
| 196 | 0.0026 | −1.40 | 208456_s_at | related RAS viral (r-ras) oncogene homolog 2 | RRAS2 | 22800 | −1 | 11p15.2 |
| 591 | 0.01 | −1.40 | 209617_s_at | catenin (cadherin-associated protein), delta 2 (neural plakophilin-related arm-repeat protein) | CTNND2 | 1501 | −1 | 5p15.2 |
| 516 | 0.01 | −1.40 | 212590_at | related RAS viral (r-ras) oncogene homolog 2 | RRAS2 | 22800 | −1 | 11p15.2 |
| 1160 | 0.02 | −1.40 | 203510_at | met proto-oncogene (hepatocyte growth factor receptor) | MET | 4233 | −1 | 7q31 |
| 1370 | 0.03 | −1.39 | 200607_s_at | RAD21 homolog (S. pombe) | RAD21 | 5885 | −1 | 8q24 |
| 843 | 0.01 | −1.39 | 212816_s_at | cystathionine-beta-synthase | CBS | 875 | −1 | 21q22.3 |
| 41 | 0.0004 | −1.39 | 216609_at | Thioredoxin | TXN | 7295 | −1 | 9q31 |
| 933 | 0.02 | −1.38 | 203414_at | monocyte to macrophage differentiation-associated | MMD | 23531 | −1 | 17q |
| 923 | 0.02 | −1.38 | 221194_s_at | PTD016 protein | LOC51136 | 51136 | −1 | 17q23.1 |
| 23 | 0.0002 | −1.37 | 202028_s_at |  |  | 6169 | −1 | 17q23-q25 |
| 309 | 0.0041 | −1.37 | 210976_s_at | phosphofructokinase, muscle | PFKM | 5213 | −1 | 12q13.3 |
| 1238 | 0.02 | −1.37 | 203685_at | B-cell CLL/lymphoma 2 | BCL2 | 596 | −1 | 18q21.33| |
| 1419 | 0.03 | −1.37 | 214519_s_at | relaxin 2 | RLN2 | 6019 | −1 | 9p24.1 |
| 251 | 0.0033 | −1.37 | 210389_x_at | tibulin, delta 1 | TUBD1 | 51174 | −1 | 17q23.1 |
| 1137 | 0.02 | −1.36 | 204237_at | GULP, engulfment adaptor PTB domain containing 1 | GULP1 | 51454 | −1 | 2q32.3-q33 |
| 51 | 0.0005 | −1.36 | 201171_at | ATPase, H+ transporting, lysosomal 9 kDa, V0 subunit e | ATP6V0E | 8992 | −1 | 5q35.1 |
| 639 | 0.01 | −1.36 | 205741_s_at | dystrobrevin, alpha | DTNA | 1837 | −1 | 18q12 |
| 1757 | 0.04 | −1.36 | 209292_at | Inhibitor of DNA binding 4, dominant negative helix loop-helix protein | ID4 | 3400 | −1 | 6p22-p21 |
| 1254 | 0.02 | −1.36 | 208078_s_at | SNF1-like kinase /// SNF1-like kinase | SNF1LK | 150094 | −1 | 21q22.3 |
| 753 | 0.01 | −1.36 | 208920_at | sorcin | SRI | 6717 | −1 | 7q21.1 |
| 7 | 0.0001 | −1.35 | 208229_at | fibroblast growth factor receptor 2 (bacteria-expressed kinase, karalinocyte growth factor receptor, or an official dysostosis 1, Crouzon syndrome, Pfeifer syndrome, Jackson-Weiss syndrome) | FGFR2 | 2263 | −1 | 10q26 |
| 715 | 0.01 | −1.35 | 36711_at | v-maf musculoaponeurotic fibrosarcoma oncogene homolog F (avian) | MAFF | 23764 | −1 | 22q13.1 |
| 1340 | 0.03 | −1.35 | 205308_at | chromosome 8 open reading frame 70 | C8orf70 | 51101 | −1 | 8q21.12 |
| 414 | 0.01 | −1.35 | 202353_s_at | proteasome (prosome, macropain) 26S subunit, non-ATPase, 12 | PSMD12 | 5718 | −1 | 17q24.2 |
| 1637 | 0.04 | −1.35 | 204348_s_at | adenylate kinase 3-like 1 | AK3L1 | 205 | −1 | 1p31.3 |
| 130 | 0.0015 | −1.35 | 218597_s_at | chromosome 10 open reading frame 70 | C10orf70 | 55847 | −1 | 10q21.1 |
| 871 | 0.02 | −1.35 | 205013_s_at | adenosine A2a receptor | ADORA2A | 135 | −1 | 22q11.23 |
| 662 | 0.01 | −1.35 | 217975_at | WW domain binding protein 5 | WBP5 | 51186 | −1 | Xq22.2 |
| 968 | 0.02 | −1.35 | 202342_s_at | tripartite motif-containing 2 | TRIM2 | 23321 | −1 | 4q31.3 |
| 477 | 0.01 | −1.34 | 201946_s_at | chaperonin containing TCP1, subunit 2 (beta) | CCT2 | 10576 | −1 | 12q15 |
| 4 | 0.0000 | −1.34 | 219138_at | ribosomal protein L14 | RPL14 | 9045 | −1 | 3p22-p21.2 |
| 1695 | 0.04 | −1.34 | 220147_s_at | family wtlh sequence similarity 60, member A | FAM60A | 58516 | −1 | 12p11 |
| 1009 | 0.02 | −1.34 | 210761_s_at | growth factor receptor-bound protein 7 | GRB7 | 2886 | −1 | 17q12 |
| 574 | 0.01 | −1.34 | 205047_s_at | asparagine synthetase | ASNS | 440 | −1 | 7q21.3 |

TABLE 5-continued

Alternative PIK 3CA gene signature
PIK3CA-GS predictor FC > 1.3 p < 0.05

| rank accord | p value | Fold Change | Probe set | Description | Gene symbol | Entrez Gene ID | Coef-fic | Cytoband |
|---|---|---|---|---|---|---|---|---|
| 1613 | 0.03 | −1.34 | 220145_at | ASAP | FLJ21159 | 79884 | −1 | 4q32.1 |
| 1077 | 0.02 | −1.34 | 221523_s_at | Ras-related GTP binding D | RRAGD | 58528 | −1 | 6q15-q16 |
| 10 | 0.0001 | −1.34 | 211406_at | immediate early response 3 interacting protein 1 | IER3IP1 | 51124 | −1 | 18q12 |
| 1902 | 0.04 | −1.34 | 204235_s_at | GULP, engulfment adaptor PTB domain containing 1 | GULP1 | 51454 | −1 | 2q32.3-q33 |
| 1420 | 0.03 | −1.33 | 205321_at | eukaryotic translation initiation factor 2, subunit 3 gamma, 52kDa | EIF2S3 | 1968 | −1 | Xp22.2-p22.1 |
| 1017 | 0.02 | −1.33 | 212690_at | DDHD domain containing 2 | DDHD2 | 23259 | −1 | 8p11.23 |
| 1922 | 0.04 | −1.33 | 219974_x_at | enoyl Coenzyme A hydratase domain containing 1 | ECHDC1 | 55862 | −1 | 6q22.33 |
| 1437 | 0.03 | −1.33 | 201161_s_at | cold shock domain protein A | CSDA | 8531 | −1 | 12p13.1 |
| 745 | 0.01 | −1.33 | 209849_s_at | RAD51 homolog C (S. cerevisiae) | RAD51C | 5889 | −1 | 17q22-q23 |
| 230 | 0.0030 | −1.33 | 205961_s_at | PC4 and SFRS1 interacting protein 1 | PSIP1 | 11168 | −1 | 9p22.3 |
| 13 | 0.0001 | −1.33 | 211212_s_at | origin recognition complex, subunit 5-like (yeast) | ORC5L | 5001 | −1 | 7q22.1 |
| 1884 | 0.04 | −1.33 | 221521_s_at | DNA replication complex GINS protein PSF2 | Pfs2 | 51659 | −1 | 16q24.1 |
| 228 | 0.0030 | −1.33 | 221326_s_at | tubulin, delta 1 | TUBD1 | 51174 | −1 | 17q23.1 |
| 767 | 0.01 | −1.32 | 213353_at | ATP-binding cassette, sub-family A (ABC1), member 5 | ABCA5 | 23461 | −1 | 17q24.3 |
| 184 | 0.0024 | −1.32 | 205361_s_at | prefoldin 4 | PFDN4 | 5203 | −1 | 20q13.2 |
| 336 | 0.0047 | −1.32 | 205543_at | heat shock 70 kDa protein 4-like | HSPA4L | 22824 | −1 | 4q28 |
| 1207 | 0.02 | −1.32 | 205573_s_at | sorting nexin 7 | SNX7 | 51375 | −1 | 1p21.3 |
| 60 | 0.0006 | −1.32 | 203565_s_at | menage a trois 1 (CAK assembly factor) | MNAT1 | 4331 | −1 | 14q23 |
| 828 | 0.01 | −1.32 | 218277_s_at | DEAH (Asp-Glu-Ala-His) box polypeptide 40 | DHX40 | 79665 | −1 | 17q23.1 |
| 1411 | 0.03 | −1.32 | 201117_s_at | carboxypeptidase E | CPE | 1363 | −1 | 4q32.3 |
| 1471 | 0.03 | −1.31 | 213548_s_at | hypothetical protein H41 | H41 | 55573 | −1 | 3q22.1 |
| 590 | 0.01 | −1.31 | 218514_at | hypothetical protein FLJ10587 | FLJ10587 | 55181 | −1 | 17q22 |
| 273 | 0.0036 | −1.31 | 205078_at | phosphatidylinositol glycan, class F | PIGF | 5281 | −1 | 2p21-p16 |
| 299 | 0.0040 | −1.31 | 204940_at | phospholamban | PLN | 5350 | −1 | 6q22.1 |
| 87 | 0.0011 | −1.31 | 221943_x_at | Ribosomal protein L38 | RPL38 | 6169 | −1 | 17q23-q25 |
| 56 | 0.0006 | −1.31 | 214553_s_at | cyclic AMP phosphoprotein, 19 kD | ARPP-19 | 10776 | −1 | 15q21.2 |
| 930 | 0.02 | −1.31 | 216693_x_at | hepatoma-derived growth factor, related protein 3 | HDGFRP3 | 50810 | −1 | 15q25.2 |
| 820 | 0.01 | 1.31 | 208729_x_at | major histocompatibility complex, class I, B | HLA-B | 3106 | 1 | 6p21.3 |
| 1259 | 0.02 | 1.31 | 218788_s_at | SET and MYND domain containing 3 | SMYD3 | 64754 | 1 | 1q44 |
| 449 | 0.01 | 1.31 | 203888_at | thrombomodulin | THBD | 7056 | 1 | 20p11.2 |
| 949 | 0.02 | 1.32 | 216250_s_at | leupaxin | LPXN | 9404 | 1 | 11q12.1 |
| 2127 | 0.05 | 1.32 | 202149_at | neural precursor cell expressed, developmentally down-regulated 9 | NEDD9 | 4739 | 1 | 6p25-p24 |
| 1288 | 0.03 | 1.32 | 38241_at | butyrophilin, subfamily 3, member A3 | BTN3A3 | 10384 | 1 | 6p21.3 |
| 1454 | 0.03 | 1.32 | 213478_at | kazrin | KIAA1026 | 23254 | 1 | 1p36.21 |
| 891 | 0.02 | 1.32 | 215536_at | major histocompatibility complex, class II, DQ beta 2 | HLA-DQB2 | 3120 | 1 | 6p21 |
| 709 | 0.01 | 1.32 | 218313_s_at | UDP-N-acetyl-alpha-D-galactosamine:polypeptide N-acetylgalactosaminyltransferase 7 (GalNAc-T7) | GALNT7 | 51809 | 1 | 4q31.1 |
| 90 | 0.0011 | 1.32 | 207291_at | proline rich Gla (G-carboxyglutamic acid) 4 (transmembrane) | PRRG4 | 79056 | 1 | 11p13 |
| 734 | 0.01 | 1.32 | 205757_at | ectonucleoside triphosphate diphosphohydrolase 5 | ENTPD5 | 957 | 1 | 14q24 |
| 119 | 0.0014 | 1.32 | 203236_s_at | lectin, galactoside-binding, soluble, 9 (galectin 9) | LGALS9 | 3965 | 1 | 17q11.2 |
| 1894 | 0.04 | 1.32 | 210538_s_at | baculoviral IAP repeat-containing 3 | BIRC3 | 330 | 1 | 11q22 |
| 556 | 0.01 | 1.32 | 212256_at | UDP-N-acetyl-alpha-D-galactosamine:polypeptide N-acetylgalactosaminyltransferase 10 (GalNAc-T10) | GALNT10 | 55568 | 1 | 5q33.2 |
| 428 | 0.01 | 1.32 | 211944_at | BAT2 domain containing 1 | BAT2D1 | 23215 | 1 | 1q23.3 |
| 393 | 0.01 | 1.33 | 206662_at | glutaredoxin (thioltransferase) | GLRX | 2745 | 1 | 5q14 |
| 1484 | 0.03 | 1.33 | 217838_s_at | Enah/Vasp-like | EVL | 51466 | 1 | 14q32.2 |
| 2130 | 0.05 | 1.33 | 209488_s_at | RNA binding protein with multiple splicing | RBPMS | 11030 | 1 | 8p12-p11 |
| 481 | 0.01 | 1.33 | 210835_s_at | C-terminal binding protein 2 | CTBP2 | 1488 | 1 | 10q26.13 |
| 482 | 0.01 | 1.34 | 212841_s_at | PTPRF interacting protein, binding protein 2 (liprin beta 2) | PPFIBP2 | 8495 | 1 | 11p15.4 |
| 221 | 0.0028 | 1.34 | 209788_s_at | type 1 tumor necrosis factor receptor shedding aminopeptidase regulator | ARTS-1 | 51752 | 1 | 5q15 |
| 2004 | 0.05 | 1.34 | 212240_s_at | phosphoinositide-3-kinase, regulatory subunit 1 | PIK3R1 | 5295 | 1 | 5q13.1 |
| 701 | 0.01 | 1.34 | 203509_at | sortilin-related receptor, L(DLR class) A repeats-containing | SORL1 | 6653 | 1 | 11q23.2-q24.2 |
| 487 | 0.01 | 1.34 | 213931_at | inhibitor of DNA binding 2, dominant negative helix loop-helix protein/// inhibitor of DNA binding 2B, dominant negative helix loop-helix protein | ID2 /// ID2B | 3398 | 1 | 2p25 /// 3p14.2 |
| 156 | 0.0019 | 1.34 | 211621_at | | AR | 367 | 1 | Xq11.2-q12 |
| 436 | 0.01 | 1.34 | 222075_s_at | ornithine decarboxylase antizyme 3 | OAZ3 | 51686 | 1 | 1q21.3 |
| 403 | 0.01 | 1.34 | 201367_s_at | zinc finger protein 36, C3H type-like 2 | ZFP36L2 | 678 | 1 | 2p22.3-p21 |
| 1382 | 0.03 | 1.34 | 217478_s_at | major histocompatibility complex, class II, DM alpha | HLA-DMA | 3108 | 1 | 6p21.3 |
| 72 | 0.0009 | 1.35 | 221041_s_at | solute carrier family 17 (anion/sugar transporter) member 5 | SLC17A5 | 26503 | 1 | 6q14-q15 |
| 1788 | 0.04 | 1.35 | 203474_at | IQ motif containing GT Pase activating protein 2 | IQGAP2 | 10788 | 1 | 5q13.3 |
| 1957 | 0.04 | 1.35 | 209522_s_at | carnitine acetyltransferase | CRAT | 1384 | 1 | 9q34.1 |
| 35 | 0.0003 | 1.35 | 203128_at | serine palmitoyltransferase, long chain base subunit 2 | SPTLC2 | 9517 | 1 | 14q24.3-q31 |
| 534 | 0.01 | 1.35 | 210139_s_at | peripheral myelin protein 22 | PMP22 | 5376 | 1 | 17p12-p11.2 |

TABLE 5-continued

Alternative PIK 3CA gene signature
PIK3CA-GS predictor FC > 1.3 p < 0.05

| rank accord | p value | Fold Change | Probe set | Description | Gene symbol | Entrez Gene ID | Coeffic | Cytoband |
|---|---|---|---|---|---|---|---|---|
| 758 | 0.01 | 1.35 | 204137_at | transmembrane 7 superfamily member 1 (upregulated in kidney) | TM7SF1 | 7107 | 1 | 1q42-q43 |
| 148 | 0.0018 | 1.35 | 269916_at | dehydrogenase E1 and transketolase domain containing 1 | DHTKD1 | 55526 | 1 | 10p14 |
| 208 | 0.0027 | 1.35 | 202421_at | immunoglobulin superfamily, member 3 | IGSF3 | 3321 | 1 | 1p13 |
| 1346 | 0.03 | 1.35 | 209276_s_at | glutaredoxin (thioltransferase) | GLRX | 2745 | 1 | 5q14 |
| 1173 | 0.02 | 1.35 | 201340_s_at | ectodermal-neural cortex (with BTB-like domain) | ENC1 | 8507 | 1 | 5q12-q13.3 |
| 976 | 0.02 | 1.35 | 211366_x_at | caspase 1, apoptosis-related cysteine peptidase (Interleukh 1, beta, convertase) | CASP1 | 834 | 1 | 11q23 |
| 824 | 0.01 | 1.35 | 205379_at | carbonyl reductase 3 | CBR3 | 874 | 1 | 21q22.2 |
| 1451 | 0.03 | 1.36 | 201976_s_at | myosin X | MYO10 | 4651 | 1 | 5p15.1-p14.3 |
| 798 | 0.01 | 1.36 | 202336_s_at | peptidylglycine alpha-amidating monooxygenase | PAM | 5066 | 1 | 5q14-q21 |
| 2028 | 0.05 | 1.36 | 202709_at | fibromodulin | FMOD | 2331 | 1 | 1q32 |
| 423 | 0.01 | 1.36 | 204875_s_at | GDP-mannose 4,6-dehydratase | GMDS | 2762 | 1 | 6p25 |
| 421 | 0.01 | 1.36 | 218322_s_at | acyl-CoA synthetase long-chain family member 5 | ACSL5 | 51703 | 1 | 10q25.1-q25.2 |
| 348 | 0.0048 | 1.36 | 221042_s_at | calmin (calponin-like, transmembrane) | CLMN | 79789 | 1 | 14q32.13 |
| 247 | 0.0033 | 1.36 | 202638_s_at | intercellular adhesion molecule 1 (CD54), human rhinovirus receptor | ICAM1 | 3383 | 1 | 19p13.3-p13.2 |
| 8 | 0.0001 | 1.36 | 212377_s_at | Notch homolog 2 (Drosophila) | NOTCH2 | 4853 | 1 | 1p13-p11 |
| 1258 | 0.02 | 1.36 | 204017_at | KDEL (Lys-Asp-Glu-Leu) endoplasmic reticulum protein retention receptor 3 | KDELR3 | 11015 | 1 | 22q13.1 |
| 102 | 0.0013 | 1.36 | 205248_at | chromosome 21 open reading frame 5 | C21orf5 | 9980 | 1 | 21q22.2 |
| 1233 | 0.02 | 1.36 | 203887_s_at | thrombomodulin | THBD | 7056 | 1 | 20p11.2 |
| 529 | 0.01 | 1.37 | 210732_s_at | lectin, galactoside-binding, soluble, 8 (galectin 8) | LGALS8 | 3964 | 1 | 1q42-q43 |
| 327 | 0.0045 | 1.37 | 213462_at | neuronal PAS domain protein 2 | NPAS2 | 4862 | 1 | 2q11.2 |
| 1908 | 0.04 | 1.37 | 210319_x_at | msh homeo box homolog 2 (Drosophila) | MSX2 | 4488 | 1 | 5q34-q35 |
| 999 | 0.02 | 1.37 | 201369_s_at | zinc finger protein 36, C3H type-like 2 | ZFP36L2 | 678 | 1 | 2p22.3-p21 |
| 495 | 0.01 | 1.37 | 208949_s_at | lectin, galactoside-binding, soluble, 3 (galectin 3) | LGALS3 /// GALIG | 3958 | 1 | 14q21-q22 |
| 769 | 0.01 | 1.37 | 209970_x_at | caspase 1, apoptosis-related cysteine peptidase | CASP1 | 834 | 1 | 11q23 |
| 986 | 0.02 | 1.37 | 204654_s_at | transcription factor AP-2 alpha (activating enhancer binding protein 2 alpha) | TFAP2A | 7020 | 1 | 6p24 |
| 32 | 0.0003 | 1.38 | 217787_s_at | UDP-N-acetyl-alpha-D-galactosamine:polypeptide N-acetylgalactosaminyltransferase 2 (GalNAc-T2) | GALNT2 | 2590 | 1 | 1q41-q42 |
| 396 | 0.01 | 1.38 | 212875_s_at | chromosome 21 open reading frame 25 | C21orf25 | 25966 | 1 | 21q22.3 |
| 1666 | 0.04 | 1.38 | 217744_s_at | PERP, TP53 apoptosis effector | PERP | 64065 | 1 | 6q24 |
| 729 | 0.01 | 1.38 | 41644_at | SAM and SH3 domain containing 1 | SASH1 | 23328 | 1 | 6q24.3 |
| 1081 | 0.02 | 1.38 | 204160_s_at | ectonucleotide pyrophosphatase/phosphodiesterase 4 (putative function) | ENPP4 | 22875 | 1 | 6p21.1 |
| 1125 | 0.02 | 1.38 | 201242_s_at | AT Pase, Na+/K+ transporting, beta 1 polypeptide | ATP1B1 | 481 | 1 | 1q24 |
| 467 | 0.01 | 1.39 | 212249_at | phosphoinositide-3-kinase, regulatory subunit 1 (p85 alpha) | PIK3R1 | 5295 | 1 | 5q13.1 |
| 297 | 0.0039 | 1.39 | 213418_at | heat shock 70 kDa protein 6 (HSP70B') | HSPA6 | 3310 | 1 | 1q23 |
| 827 | 0.01 | 1.39 | 202962_at | kinesin family member 13B | KIF13B | 23303 | 1 | 8p12 |
| 290 | 0.0039 | 1.39 | 222258_s_at | SH3-domain binding protein 4 | SH3BP4 | 23677 | 1 | 2q37.1-q37.2 |
| 551 | 0.01 | 1.39 | 214130_s_at | phosphodiesterase 4D interacting protein (myomegadin) | PDE4DIP | 9659 | 1 | 1q12 |
| 1655 | 0.04 | 1.39 | 204365_s_at | chromosome 2 open reading frame 23 | C2orf23 | 65055 | 1 | 2p11.2 |
| 1533 | 0.03 | 1.39 | 205668_at | lymphocyte antigen 75 | LY75 | 4065 | 1 | 2q24 |
| 143 | 0.0017 | 1.39 | 218451_at | CUB domain containing protein 1 | CDCP1 | 64866 | 1 | 3p21.31 |
| 948 | 0.02 | 1.40 | 205225_at | estrogen receptor 1 | ESR1 | 2099 | 1 | 6q25.1 |
| 610 | 0.01 | 1.40 | 211965_at | zinc finger protein 36, C3H type-like 1 | ZFP36L1 | 677 | 1 | 14q22-q24 |
| 511 | 0.01 | 1.40 | 213308_at | SH3 and multiple ankyrin repeat domains 2 | SHANK2 | 22941 | 1 | 11q13.3-q13.4 |
| 1018 | 0.02 | 1.40 | 208006_at | forkhead box I1 | FOXI1 | 2299 | 1 | 5q34 |
| 1374 | 0.03 | 1.40 | 206191_at | ectonucleoside triphosphate diphosphohydrolase 3 | ENTPD3 | 956 | 1 | 3p21.3 |
| 950 | 0.02 | 1.40 | 220108_at | guanine nucleotide binding protein (G protein), alpha 14 | GNA14 | 9630 | 1 | 9q21 |
| 964 | 0.02 | 1.40 | 211368_s_at | caspase 1, apoptosis-related cysteine peptidase | CASP1 | 834 | 1 | 11q23 |
| 100 | 0.0013 | 1.40 | 208683_at | calpain 2, (m/II) large subunit | CAPN2 | 824 | 1 | 1q41-q42 |
| 1927 | 0.04 | 1.41 | 214295_at | KIAA0485 protein | KIAA0485 | 57235 | 1 | — |
| 561 | 0.01 | 1.41 | 39549_at | neuronal PAS domain protein 2 | NPAS2 | 4862 | 1 | 2q11.2 |
| 236 | 0.0031 | 1.41 | 214129_at | Phosphodiesterase 4D interacting protein (myomegadin) | PDE4DIP | 9659 | 1 | 1q12 |
| 963 | 0.02 | 1.41 | 204446_s_at | arachidonate 5-lipoxygenase | ALOX5 | 240 | 1 | 10q11.2 |
| 317 | 0.0043 | 1.41 | 206011_at | caspase 1, apoptosis-related cysteine peptidase | CASP1 | 834 | 1 | 11q23 |
| 803 | 0.01 | 1.41 | 205879_x_at | ret proto-oncogene (multiple endocrine neoplasta and medulary thyroid carcinoma 1, Hirshsprung disease) | RET | 5979 | 1 | 10q11.2 |
| 49 | 0.0005 | 1.41 | 220066_at | caspase recruitment domain family, member 15 | CARD15 | 64127 | 1 | 16q21 |
| 1151 | 0.02 | 1.42 | 221558_s_at | lymphoid enhancer-binding factor 1 | LEF1 | 51176 | 1 | 4q23-q25 |
| 480 | 0.01 | 1.42 | 211110_s_at | androgen receptor (dihydrotestosterone receptor testicular ferminization; spinal and bulbar muscular atrophy; Kennedy disease) | AR | 367 | 1 | Xq11.2-q12 |
| 1594 | 0.03 | 1.42 | 201641_at | bone marrow stromal cell antigen 2 | BST2 | 684 | 1 | 19p13.2 |

TABLE 5-continued

Alternative PIK 3CA gene signature
PIK3CA-GS predictor FC > 1.3 p < 0.05

| rank accord | p value | Fold Change | Probe set | Description | Gene symbol | Entrez Gene ID | Coef-fic | Cytoband |
|---|---|---|---|---|---|---|---|---|
| 416 | 0.01 | 1.42 | 208997_s_at | uncoupling protein 2 (mitochondrial, proton carrier) | UCP2 | 7351 | 1 | 11q13 |
| 306 | 0.0041 | 1.43 | 218273_s_at | protein phosphatase 2C, magnesium-dependent, catalytic subunit | PPM2C | 54704 | 1 | 8q22.1 |
| 22 | 0.0002 | 1.43 | 213109_at | TRAF2 and NCK interacting kinase | TNIK | 23043 | 1 | 3q26.2-q26.31 |
| 998 | 0.02 | 1.43 | 203221_at | transducin-like enhancer of split 1 (E(sp1) homolog Droxophia) | TLE1 | 7088 | 1 | 9q21.32 |
| 1840 | 0.04 | 1.43 | 212551_at | CAP, adenylate cyclase-associated protein, 2 (yeast) | CAP2 | 10486 | 1 | 6p22.3 |
| 2023 | 0.05 | 1.44 | 200606_at | desmoplakin | DSP | 1832 | 1 | 6p24 |
| 110 | 0.0013 | 1.44 | 201482_at | quiescin Q6 | QSCN6 | 5768 | 1 | 1q24 |
| 341 | 0.0047 | 1.44 | 218918_at | mannosidase, alpha, class 1C, member 1 | MAN1C1 | 57134 | 1 | 1p35 |
| 892 | 0.02 | 1.45 | 214329_x_at | Tumor necrosis factor (ligand) superfamily, member/// Tumor necrosis factor (ligand) superfamily, member 10 | TNFSF10 | 8743 | 1 | 3q26 |
| 719 | 0.01 | 1.45 | 213236_at | SAM and SH3 domain containing 1 | SASH1 | 23328 | 1 | 6q24.3 |
| 168 | 0.0021 | 1.45 | 218084_x_at | FXYD domain containing ion transport regulator 5 | FXYD5 | 53827 | 1 | 19q12-q13.1 |
| 386 | 0.01 | 1.46 | 202017_at | epoxide hydrolase 1, microsomal (xenobiotic) | EPHX1 | 2052 | 1 | 1q42.1 |
| 17 | 0.0001 | 1.46 | 212415_at | septin 6 | 40062 | 23157 | 1 | Xq24 |
| 1672 | 0.04 | 1.46 | 212543_at | absent in melanoma 1 | AIM1 | 202 | 1 | 6q21 |
| 479 | 0.01 | 1.47 | 202286_s_at | tumor-associated calcium signal transducer 2 | TACSTD2 | 4070 | 1 | 1p32-p31 |
| 232 | 0.0030 | 1.47 | 209619_at | CD74 antigen (invariant polypeptide of major histocompatibility complex, class II antigen-associated) | CD74 | 972 | 1 | 5q32 |
| 249 | 0.0033 | 1.47 | 204352_at | TNF receptor-associated factor 5 | TRAF5 | 7188 | 1 | 1q32 |
| 219 | 0.0028 | 1.47 | 214791_at | hypothetical protein BC004921 | LOC93349 | 93349 | 1 | 2q37.1 |
| 20 | 0.0002 | 1.47 | 202743_at | phosphoinositide-3-kinase, regulatory subunit 3 (p55, gamma) | PIK3R3 | 8503 | 1 | 1p34.1 |
| 1140 | 0.02 | 1.47 | 205472_s_at | dachshund homolog 1 (Drosophila) | DACH1 | 1602 | 1 | 13q22 |
| 356 | 0.00 | 1.48 | 204983_s_at | glypican 4 | GPC4 | 2239 | 1 | Xq26.1 |
| 613 | 0.01 | 1.49 | 213107_at | TRAF2 and NCK interacting kinase | TNIK | 23043 | 1 | 3q26.2-q26.31 |
| 30 | 0.0003 | 1.49 | 201288_at | Rho GDP dissociation inhibitor (GDI) beta | ARHGDIB | 397 | 1 | 12p12.3 |
| 1116 | 0.02 | 1.49 | 221841_s_at | Kruppel-like factor 4 (gut) | KLF4 | 9314 | 1 | 9q31 |
| 1032 | 0.02 | 1.49 | 202986_at | aryl-hydrocarbon receptor nuclear translocator 2 | ARNT2 | 9915 | 1 | 15q24 |
| 1630 | 0.03 | 1.49 | 1405_i_at | chemokine (C-C motif) ligand 5 | CCL5 | 6352 | 1 | 17q11.2-q12 |
| 862 | 0.02 | 1.50 | 205645_at | RALBP1 associated Eps domain containing 2 | REPS2 | 9185 | 1 | Xp22.2-p22.13 |
| 1231 | 0.02 | 1.50 | 217966_s_at | chromosome 1 open reading frame 24 | C1orf24 | 116496 | 1 | 1q25 |
| 1549 | 0.03 | 1.51 | 210372_s_at | tumor protein D52-like 1 | TPD52L1 | 7164 | 1 | 6q22-q23 |
| 1456 | 0.03 | 1.53 | 202376_at | serpin peptidase inhibitor, clade A (alpha-1 antiproteinase, antitrypsin), member 3 | SERPINA3 | 12 | 1 | 14q32.1 |
| 821 | 0.01 | 1.53 | 205278_at | glutamate decarboxylase 1 (brain, 67 kDa) | GAD1 | 2571 | 1 | 2q31 |
| 59 | 0.0006 | 1.54 | 208502_s_at | paired-like homeodomain transcription factor 1 | PITX1 | 5307 | 1 | 5q31 |
| 321 | 0.0044 | 1.54 | 200824_at | glutathione S-transferase pi | GSTP1 | 2950 | 1 | 11q13 |
| 342 | 0.0047 | 1.55 | 212325_at | KIAA1102 protein | KIAA1102 | 22998 | 1 | 4p13 |
| 126 | 0.0015 | 1.55 | 208998_at | uncoupling protein 2 (mitochondrial, proton carrier) | UCP2 | 7351 | 1 | 11q13 |
| 1358 | 0.03 | 1.56 | 217967_s_at | chromosome 1 open reading frame 24 | C1orf24 | 116496 | 1 | 1q25 |
| 817 | 0.01 | 1.56 | 203786_s_at | tumor protein D52-like 1 | TPD52L1 | 7164 | 1 | 6q22-q23 |
| 776 | 0.01 | 1.57 | 205990_s_at | wingless-type MMTV integration site family, member 5A | WNT5A | 7474 | 1 | 3p21-p14 |
| 1462 | 0.03 | 1.57 | 205471_s_at | dachshund homolog 1 (Drosophila) | DACH1 | 1602 | 1 | 13q22 |
| 1748 | 0.04 | 1.57 | 203354_s_at | pleckstrin and Sec7 domain containing 3 | PSD3 | 23362 | 1 | 8pter-p23.3 |
| 967 | 0.02 | 1.58 | 202687_s_at | tumor necrosis factor (ligand) superfamily, member 10/// tumor necrosis factor (ligand) superfamily, member 10 | TNFSF10 | 8743 | 1 | 3q26 |
| 1328 | 0.03 | 1.59 | 218613_at | pleckstrin and Sec7 domain containing 3 | PSD3 | 23362 | 1 | 8pter-p23.3 |
| 372 | 0.01 | 1.60 | 204972_at | 2'-5'-oligoadenylate synthetase 2, 69/71 kDa | OAS2 | 4939 | 1 | 12q24.2 |
| 144 | 0.0017 | 1.62 | 204984_at | glypican 4 | GPC4 | 2239 | 1 | Xq26.1 |
| 291 | 0.0039 | 1.62 | 202688_at | tumor necrosis factor (ligand) superfamily, member 10/// tumor necrosis factor (ligand) superfamily, member 10 | TNFSF10 | 8743 | 1 | 3q26 |
| 1475 | 0.03 | 1.62 | 214774_x_at | trinucleotide repeat containing 9 | TNRC9 | 27324 | 1 | 16q12.1 |
| 85 | 0.0010 | 1.63 | 221666_s_at | PYD and CARD domain containing | PYCARD | 29108 | 1 | 16p12-p11.2 |
| 530 | 0.01 | 1.63 | 203649_s_at | phospholipase A2, group IIA (platelets, synovial fluid) | PLA2G2A | 5320 | 1 | 1p35 |
| 46 | 0.0004 | 1.67 | 211828_s_at | TRAF2 and NCK interacting kinase | TNIK | 23043 | 1 | 3q26.2-q26.31 |
| 151 | 0.0018 | 1.70 | 212327_at | KIAA1102 protein | KIAA1102 | 22998 | 1 | 4p13 |
| 86 | 0.0011 | 1.70 | 204070_at | retinoic acid receptor responder (tazarotene induced) 3 | RARRES3 | 5920 | 1 | 11q23 |
| 1656 | 0.04 | 1.70 | 220177_s_at | transmembrane protease, serine 3 | TMPRSS3 | 64699 | 1 | 21q22.3 |
| 1538 | 0.03 | 1.71 | 214440_at | N-acetyltransferase 1 (arylamine N-acetyltransferase) | NAT1 | 9 | 1 | 8p23.1-p21.3 |
| 167 | 0.0021 | 1.71 | 212328_at | KIAA1102 protein | KIAA1102 | 22998 | 1 | 4p13 |
| 1514 | 0.03 | 1.72 | 203355_s_at | pleckstrin and Sec7 domain containing 3 | PSD3 | 23362 | 1 | 8pter-p23.3 |
| 736 | 0.01 | 1.73 | 201860_s_at | plasminogen activator, tissue | PLAT | 5327 | 1 | 8p12 |
| 265 | 0.0035 | 1.74 | 219630_at | PDZK1 interacting protein 1 | PDZK1IP1 | 10158 | 1 | 1p33 |
| 1469 | 0.03 | 1.75 | 209016_s_at | keratin 7 | KRT7 | 3855 | 1 | 12q12-q13 |
| 391 | 0.01 | 1.76 | 204364_s_at | chromosome 2 open reading frame 23 | C2orf23 | 65055 | 1 | 2p11.2 |
| 106 | 0.0013 | 1.80 | 219850_s_at | ets homologous factor | EHF | 26298 | 1 | 11p12 |

TABLE 5-continued

Alternative PIK 3CA gene signature
PIK3CA-GS predictor FC > 1.3 p < 0.05

| rank accord | p value | Fold Change | Probe set | Description | Gene symbol | Entrez Gene ID | Coef-fic | Cytoband |
|---|---|---|---|---|---|---|---|---|
| 28 | 0.0003 | 1.82 | 217771_at | golgi phosphoprotein 2 | GOLPH2 | 51280 | 1 | 9q21.33 |
| 179 | 0.0023 | 1.84 | 214428_x_at | complement component 4A /// complement component 4B/// complement component 4B, telomeric | C4A /// C4B | 720 | 1 | 6p21.3 |
| 172 | 0.0021 | 1.84 | 213693_s_at | mucin 1, transmembrane | MUC1 | 4582 | 1 | 1q21 |
| 260 | 0.0034 | 1.90 | 207847_s_at | mucin 1, transmembrane | MUC1 | 4582 | 1 | 1q21 |
| 193 | 0.0025 | 1.92 | 208451_s_at | complement component 4A /// complement component 4B/// complement component 4B, telomeric | C4A /// C4B | 721 | 1 | 6p21.3 |
| 5 | 0.0000 | 1.96 | 206994_at | cystatin S | CST4 | 1472 | 1 | 20p11.21 |
| 244 | 0.0032 | 1.97 | 219759_at | leukocyte-derived arginine aminopeptidase | LRAP | 64167 | 1 | 5q15 |
| 392 | 0.01 | 1.98 | 202357_s_at | B-factor, properdin | BF | 629 | 1 | 6p21.3 |
| 117 | 0.0014 | 2.01 | 209706_at | NK3 transcription factor related, locus 1 (*Drosophila*) | NKX3-1 | 4824 | 1 | 8p21 |
| 328 | 0.0045 | 2.12 | 220414_at | calmodulin-like 5 | CALML5 | 51806 | 1 | 10p15.1 |
| 1343 | 0.03 | 2.15 | 206204_at | growth factor receptor-bound protein 14 | GRB14 | 2888 | 1 | 2q22-q24 |
| 614 | 0.01 | 2.16 | 201884_at | carcinoembryonic antigen-related cell adhesion molecule 5 3-hydroxy-3-methylgluteryl-Coenzyme A synthase 2 | CEACAM5 | 1048 | 1 | 19q13.1-q13.2 |
| 476 | 0.01 | 2.23 | 204607_at | 3-hydroxy-3-methylglutaryl-Coenzyme A synthase 2 (mitochondrial) | HMGCS2 | 3158 | 1 | 1p13-p12 |
| 541 | 0.01 | 2.34 | 211657_at | carcinoembryonic antigen-related cell adhesion molecule 6 (non-specific cross reacting antigen)/// carcinoembryonic antigen-related cell adhesion molecule 6 (non-specific cross reacting antigen) | CEACAM6 | 4680 | 1 | 19q13.2 |
| 911 | 0.02 | 2.34 | 203757_s_at | carcinoembryonic antigen-related cell adhesion molecule 6 (non-specific cross reacting antigen) | CEACAM6 | 4680 | 1 | 19q13.2 |
| 258 | 0.0034 | 3.23 | 202018_s_at | lactotransferrin | LTF | 4057 | 1 | 3p21.31 |
| 37 | 0.0003 | 4.47 | 206799_at | secretoglobin, family 1D, member 2 | SCGB1D2 | 10647 | 1 | 11q13 |
| 6 | 0.0001 | 5.19 | 206378_at | secretoglobin, family 2A, member 2 | SCGB2A2 | 4250 | 1 | 11q13 |

TABLE 6

Most preferred genes associated with PIK3CA mutation

| Probe Set ID | Gene Symbol | Gene Title | Entrez Gene ID | Cytoband |
|---|---|---|---|---|
| 201288_at | ARHGDIB | Rho GDP dissociation inhibitor (GDI) beta | 397 | 12p12.3 |
| 214553_s_at | ARPP-19 | cyclic AMP phosphoprotein, 19 kD | 10776 | 15q21.2 |
| 221586_s_at | E2F5 | E2F transcription factor 5, p130-binding | 1875 | 8q21.2 |
| 217787_s_at | GALNT2 | UDP-N-acetyl-alpha-D-galactosamine:polypeptide N-acetylgalactosaminyltransferase 2 (GalNAc-T2) | 2590 | 1q41-q42 |
| 217771_at | GOLM1 | golgi membrane protein 1 | 51280 | 9q21.33 |
| 203565_s_at | MNAT1 | menage a trois homolog 1, cyclin H assembly factor (*Xeopus laevis*) | 4331 | 14q23 |
| 202431_s_at | MYC | v-myc myelocytomatosis viral oncogene homolog (avian) | 4609 | 8q24.21 |
| 212377_s_at | NOTCH2 | Notch homolog 2 (Drosophila) | 4853 | 1p13-p11 |
| 211212_s_at | ORC5L | origin recognition complex, subunit 5-like (yeast) | 5001 | 7q22.1 |
| 204992_s_at | PFN2 | profilin 2 | 5217 | 3q25.1-q25.2 |
| 202743_at | PIK3R3 | phosphoinositide-3-kinase, regulatory subunit 3 (gamma) | 8503 | 1p34.1 |
| 206378_at | SCGB2A2 | secretoglobin, family 2A, member 2 | 4250 | 11q13 |
| 203128_at | SPTLC2 | serine palmitoyltransferase, long chain base subunit 2 | 9517 | 14q24.3-q31 |
| 211828_s_at | TNIK | TRAF2 and NCK interacting kinase | 23043 | 3q26.2-q26.31 |

The invention claimed is:

1. A method to determine a signature of PIK3CA for treatment of early stage breast cancer in a patient, the method comprising:
   measuring an expression level of genes from a biopsy of a breast cancer tumour from the patient by contacting mRNA sequences from the cells of the said biopsy with a gene set of at least 3 capture nucleotide sequences that specifically hybridizes to RNA encoded by ARHGDIB, GALNT2 and PFN2 of a breast cell;
   determining the PIK3CA signature for said tumour, wherein under-expression of ARHGDIB and GALNT2 and/or overexpression of PFN2 corresponds to a wild-type PIK3CA signature; and
   administering to a patient comprising a breast cancer tumour having a wild-type PIK3CA signature a PI3-kinase inhibitor or a PI3-kinase pathway inhibitor.

2. The method of claim 1, wherein the gene set further comprises one or more capture nucleotide sequences selected from the sequences of Table 6.

3. The method of claim 1 further comprising a step of sequencing of the PIK3CA gene.

4. The method of claim 1 further comprising a step of determining a clinical outcome of breast tumour affecting a patient if treated with an antitumoural agent against breast tumour.

5. The method according to claim 4 wherein the breast tumour is ER+.

6. The method according to the claim 5 wherein the breast tumour is obtained from a high proliferative tumour sample.

7. The method according to the claim 5 wherein the breast tumour is a luminal B ER+ tumour.

8. The method of claim 7, wherein the breast tumor harbours overexpression of ARHGDIB and GALNT2 and/or under-expression of PFN2 and which further comprises a step of administering to the patient, an anti-oestrogen agent selected from the group consisting of tamoxifen, raloxifene, faslodex and a mixture thereof.

9. The method according to claim 5, further comprising a step of administering to the patient an anti oestrogen agent selected from the group consisting of a selective oestrogen receptor modulator, a selective oestrogen receptor down regulator, a GnRH analog, and an aromatase inhibitor.

10. The method of claim 5, wherein the breast tumor harbours overexpression of ARHGDIB and GALNT2 and/or under-expression of PFN2 and which further comprises a step of administering to the patient an anti-oestrogen agent selected from the group consisting of tamoxifen, raloxifene, faslodex, and a mixture thereof.

11. The method according to claim 5, wherein the breast tumor harbours overexpression of ARHGDIB and GALNT2 and/or under-expression of PFN2 and wherein the breast tumor is Her2+, and which further comprises a step of administering to the patient an antitumoral agent selected from the group consisting of a selective oestrogen receptor modulator, a selective oestrogen receptor down regulator, a GnRH analog, and an aromatase inhibitor.

12. The method of claim 11 wherein the antitumoral agent further comprise an anti Her2 compound.

13. The method of claim 12, wherein the anti Her2 compound is an anti Her2 antibody.

14. The method of claim 13, wherein the anti Her2 compound is Trastuzumab.

15. The method of claim 1, wherein the inhibitor of the PI3-kinase pathway is a mTOR inhibitor.

16. The method of claim 15, wherein the mTOR inhibitor is Everolimus.

17. The method according to claim 4, wherein the breast tumor harbours overexpression of ARHGDIB and GALNT2 and/or under-expression of PFN2 and wherein the breast tumor is Her2+, and which further comprises a step of administering to the patient an antitumoral agent being an anti Her2 compound.

18. The method of claim 17, wherein the anti Her2 compound is an anti Her2 antibody.

19. The method of claim 18, wherein the anti Her2 antibody is Trastuzumab.

20. The method according to claim 5, wherein the breast tumor harbours a wild-type PIK3CA signature and which further comprises a step of administering to the patient a chemotherapy.

21. The method according to claim 5, wherein the breast tumor harbours a wild-type PIK3CA signature and which further comprises a step of administering to the patient a radiotherapy.

22. The method of claim 1, wherein the expression level of up to 81 genes is measured.

23. The method of claim 1, wherein the breast cancer tumor is less than 2 cm and/or the patient has a negative lymph node status.

* * * * *

SEQUENCE LISTING

<160> NUMBER OF SEQ ID NOS: 6

<210> SEQ ID NO 1
<211> LENGTH: 21
<212> TYPE: DNA
<213> ORGANISM: Artificial sequence
<220> FEATURE:
<223> OTHER INFORMATION: Akt1 primer, Exon 4 Forward

```
<400> SEQUENCE: 1
agggtctgac ccctagagat g                                              21

<210> SEQ ID NO 2
<211> LENGTH: 18
<212> TYPE: DNA
<213> ORGANISM: Artificial sequence
<220> FEATURE:
<223> OTHER INFORMATION: Akt1 Exon 4 Reverse primer

<400> SEQUENCE: 2
agagggctcc agccaacc                                                  18

<210> SEQ ID NO 3
<211> LENGTH: 24
<212> TYPE: DNA
<213> ORGANISM: Artificial Sequence
<220> FEATURE:
<223> OTHER INFORMATION: PIK3CA Exon 9 Forward primer
<220> FEATURE:
<221> NAME/KEY: misc_feature
<222> LOCATION: (1)..(1)
<223> OTHER INFORMATION: FAM
<220> FEATURE:
<221> NAME/KEY: misc_feature
<222> LOCATION: (1)..(1)
<223> OTHER INFORMATION: 6-FAM

<400> SEQUENCE: 3
tgaaaatgta tttgcttttt ctgt                                           24

<210> SEQ ID NO 4
<211> LENGTH: 24
<212> TYPE: DNA
<213> ORGANISM: Artificial Sequence
<220> FEATURE:
<223> OTHER INFORMATION: PIK3CA Exon 9 Reverse primer
<220> FEATURE:
<221> NAME/KEY: misc_feature
<222> LOCATION: (1)..(1)
<223> OTHER INFORMATION: VIC

<400> SEQUENCE: 4
tgtaaattct gctttattta ttcc                                           24

<210> SEQ ID NO 5
<211> LENGTH: 23
<212> TYPE: DNA
<213> ORGANISM: Artificial Sequence
<220> FEATURE:
<223> OTHER INFORMATION: PIK3CA Exon 20 Forward primer
<220> FEATURE:
<221> NAME/KEY: misc_feature
<222> LOCATION: (1)..(1)
<223> OTHER INFORMATION: NED

<400> SEQUENCE: 5
tccaaactga ccaaactgtt ctt                                            23

<210> SEQ ID NO 6
<211> LENGTH: 24
<212> TYPE: DNA
<213> ORGANISM: Artificial Sequence
<220> FEATURE:
<223> OTHER INFORMATION: PIK3CA Exomn 20 Reverse Primer
<220> FEATURE:
<221> NAME/KEY: misc_feature
<222> LOCATION: (1)..(1)
<223> OTHER INFORMATION: PET
```

```
<220> FEATURE:
<221> NAME/KEY: misc_feature
<222> LOCATION: (1)..(1)
<223> OTHER INFORMATION: PE

<400> SEQUENCE: 6
tccagagtga gctttcattt tctc                                            24
```